(12) United States Patent
Tjulandin et al.

(10) Patent No.: US 9,957,236 B2
(45) Date of Patent: May 1, 2018

(54) SELECTIVE INHIBITORS INTERFERING WITH FIBROBLAST GROWTH FACTOR RECEPTOR AND FRS2 INTERACTION FOR THE PREVENTION AND TREATMENT OF CANCER AND OTHER DISEASES

(71) Applicant: LIMITED LIABILITY COMPANY "RUSSIAN PHARMACEUTICAL TECHNOLOGIES", St.Petersburg (RU)

(72) Inventors: Sergey Alexeevich Tjulandin, Moscow (RU); Mikhail Yur'evich Byakhov, Moscow (RU); Ilya Valer'evich Tsimafeyeu, Moscow (RU)

(73) Assignee: LIMITED LIABILITY COMPANY "RUSSIAN PHARMACEUTICAL TECHNOLOGIES", St. Petersburg (RU)

( * ) Notice: Subject to any disclaimer, the term of this patent is extended or adjusted under 35 U.S.C. 154(b) by 0 days. days.

(21) Appl. No.: 15/355,506

(22) Filed: Nov. 18, 2016

(65) Prior Publication Data

US 2017/0183315 A1 Jun. 29, 2017

Related U.S. Application Data

(63) Continuation of application No. PCT/EA2014/000013, filed on Jun. 6, 2014.

(30) Foreign Application Priority Data

May 22, 2014 (EA) .................................. 201400495

(51) Int. Cl.
| | |
|---|---|
| *A61K 31/505* | (2006.01) |
| *C07D 239/42* | (2006.01) |
| *C07D 213/42* | (2006.01) |
| *A61K 31/4418* | (2006.01) |
| *C07D 239/26* | (2006.01) |

(52) U.S. Cl.
CPC ........ *C07D 239/42* (2013.01); *A61K 31/4418* (2013.01); *A61K 31/505* (2013.01); *C07D 213/42* (2013.01); *C07D 239/26* (2013.01)

(58) Field of Classification Search
CPC .. C07D 213/34; C07D 239/42; A61K 31/435; A61K 31/495; A61K 31/505
USPC .................... 544/335; 546/331; 514/256, 357
See application file for complete search history.

(56) References Cited

U.S. PATENT DOCUMENTS

| | | | |
|---|---|---|---|
| 439,179 | A | 10/1890 | Pederson |
| 3,773,919 | A | 11/1973 | Boswell et al. |
| 4,485,045 | A | 11/1984 | Regen |
| 4,544,545 | A | 10/1985 | Ryan et al. |
| 5,013,556 | A | 5/1991 | Woodle et al. |
| 2009/0005410 | A1 | 1/2009 | Charvat et al. |
| 2012/0277295 | A1 | 11/2012 | Ekimoto |
| 2012/0329861 | A1 | 12/2012 | Brooks et al. |

FOREIGN PATENT DOCUMENTS

| | | | |
|---|---|---|---|
| WO | 02068406 | A2 | 9/2002 |
| WO | 2004013091 | A2 | 2/2004 |
| WO | 2004087814 | A1 | 10/2004 |
| WO | WO 2012/015723 | * | 2/2012 |

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*
Stepanova et al., Abstract No. e22097 (J Clin Oncol. 31) 2013.*
Abuharbeid et al., "The fibroblast growth factor-binding protein FGF-BP", The International Journal of Biochemistry & Cell Biology, 2006, vol. 38, pp. 1463-1468.
Arai et al., "Fibroblast Growth Factor Receptor 2 Tyrosine Kinase Fusions Define a Unique Molecular Subtype of Cholangiocarcinoma", Hepatology, Official Journal of the American Association for the Study of Liver Deseases, 2014, pp. 1427-1434.
Ayers et al., "Discovery and Validation of Biomarkers that Respond to Treatment with Brivanib Alaninate, a Small-Molecule VEGFR-2/FGFR-1 Antagonist", Cancer Research, 2007, vol. 67, pp. 6899-6906.
Beenken et al., "The FGF family: biology, pathophysiology and therapy", National Institute of Health, Author Manuscript, Nat Rev Drug Discov., 2013, pp. 1-42.
Brooks et al., "Molecular Pathways: Fibroblast Growth Factor Signaling: A New Therapeutic Opportunity in Cancer", Clinical Cancer Research, 2012, vol. 18, No. 7, pp. 1855-1862.
Chang et al., "Prognostic Value of FGFR Gene Amplification in Patients with Different Types of Cancer: A Systematic Review and Meta-Analysis", PLOS ONE, 2014, vol. 9, Issue 8, pp. 1-8.
Dienstmann et al., "Genomic aberrations in the FGFR pathway: opportunities for targeted therapies in solid tumors", Annals of Oncology, 2013, pp. 1-12.
Eswarakumar et al., "Cellular signaling by fibroblast growth factor receptors", Cytokine & Growth Factor Reviews, 2005, vol. 16, pp. 139-149.

(Continued)

*Primary Examiner* — Deepak R Rao
(74) *Attorney, Agent, or Firm* — BCF LLP

(57) ABSTRACT

The present technology relates to medicine and includes the use of inhibitors which selectively interfere with the interaction between a fibroblast growth factor receptor and FRS2, and with the interaction with other components of the FRS2 complex. Use of the selective inhibitors described in the present technology leads to a proven increase in anti-tumor efficacy relative to other inhibitors and monoclonal antibodies, a decrease in the toxicity of treatment, and the possibility of achieving complete blockage using a low agent concentration and of conducting long-term treatment. The advantage of the technology includes the development of a novel class of medicinal agents for treating malignant neoplasms and other diseases.

10 Claims, 16 Drawing Sheets

(56) References Cited

OTHER PUBLICATIONS

Folkman et al., "Induction of angiogenesis during the transition from hyperplasia to neoplasia", Macmillan Magazines Ltd., 1989, pp. 1-4.
Gavine et al., "AZD4547: An Orally Bioavailable, Potent, and Selective Inhibitor of the Fibroblast Growth Factor Receptor Tyrosine Kinase Family", Cancer Research, 2012, vol. 72, No. 8, pp. 2045-2056.
Gozgit et al., "Ponatinib (AP24534), a Multitargeted Pan-FGFR Inhibitor with Activity in Multiple FGFR-Amplified or Mutated Cancer Models", Molecular Cancer Therapeutics, 2012, vol. 11, No. 3, pp. 690-699.
Gust et al., "Fibroblast Growth Factor Receptor 3 is a Rational Therapeutic Target in Bladder Cancer", National Institute of Health, Author Manuscript, Mol Cancer Ther., 2014, pp. 1-17.
(Book) Gosselin et al. (as reviewed by D. R. Laurence in "Book Reviews", p. 193), "Clinical Toxicology of CommercialProducts. Acute Poisoning, 4th edition", 1976, 427 p.
Abstract—Heroult et al., "Fibroblast Growth Factor Receptor Signaling in Cancer Biology and Treatment", Current Signal Transduction Therapy, 2014, vol. 9, No. 1, pp. 15-25(11).
Hurwitz, "Specific and Nonspecific Macromolecule-Drug Conjugates for the Improvement of Cancer chemotherapy", Biopolymers, 1983, vol. 22, pp. 557-567.
Huynh et al., "Brivanib Alaninate, a Dual Inhibitor of Vascular Endothelial Growth Factor Receptor and Fibroblast Growth Factor Receptor Tyrosine Kinases, Induces Growth Inhibition in Mouse Models of Human Hepatocellular Carcinoma", Clinical Cancer Research, 2008 vol. 14, No. 19, pp. 6146-6153.
Hwang et al., "Hepatic uptake and degradation of unilamellar sphingomyelin/cholesterol liposomes: A kinetic study", Ppoc. Natl. Acad. Sci. USA, 1980, vol. 77, No. 7, pp. 4030-4034.
Kouhara et al., "A Lipid-Anchored Grb2-Binding Protein That Links FGF-Receptor Activation to the Ras/MAPK Signaling Pathway", Cell Press, 1997, vol. 89, pp. 693-702.
Langer et al., "Biocompatibility of polymeric delivery systems for macromolecules", Journal of Biomedical Materials Research, 1981, vol. 15, pp. 267-277.
Ong et al., "FRS2 Proteins Recruit Intracellular Signaling Pathways by Binding to Diverse Targets on Fibroblast Growth Factor and Nerve Growth Factor Receptors", Molecular and Cellular Biology, 2000, vol. 20, No. 3, pp. 979-989.
Abstract—Passaniti et al., "A simple, quantitative method for assessing angiogenesis and antiangiogenic agents using reconstituted basement membrane, heparin, and fibroblast growth factor.", Lab. Invest., 1992, vol. 67, No. 4, pp. 519-528.
Squires et al., "Potent, Selective Inhibitors of Fibroblast Growth Factor Receptor Define Fibroblast Growth Factor Dependence in Preclinical Cancer Models", Molecular Cancer Therapeutics, 2011, vol. 10, No. 9, pp. 1542-1552.
Eppstein et al., "Biological activity of liposome-encapsulated murine interferon y is mediated by a cell membrane receptor", Ppoc. Natl. Acad. Sci. USA, 1985, vol. 82, pp. 3688-3692.
Sarker et al., "A Phase I Pharmacokinetic and Pharmacodynamic Study of TKI258, an Oral, Multitargeted Receptor Tyrosine Kinase Inhibitor in Patients with Advanced Solid Tumors", Clinical Cancer Research, 2008 vol. 14, No. 7, pp. 2075-2081.
Sidman et al., "Biodegradable, Implantable Sustained Release Systems based on Glutamic Acid Copolymers", Journal of Membrane Science, 1980, vol. 7, pp. 277-291.
Abstract—Izmerov et al., Toxicometry characteristics of the industrial poisons in a single exposure (reference book), "MEDICINA", 1977, p. 240, УДК 616.63-(031).
Abstract—Stepanova et al., "Targeting angiogenesis driven by fibroblast growth factor using RPT835, an FGFR2 inhibitor", J Clinoncol, 2013, http://meetinglibrary.asco.org/content/116060-132.
Tannheimer et al., "Characterization of fibroblast growth factor receptor 2 overexpression in the human breast cancer cell line SUM-52PE", Breast Cancer Research, 2000, vol. 2, No. 4, pp. 311-320.
Tenhagen, "Fibroblast growth factor receptors in breast cancer: expression, downstream effects, and possible drug targets", Endocrine-Related Cancer, 2012, vol. 19, pp. R115-R129.
Tomlinson et al., "Altered Splicing of FGFR1 Is Associated with High Tumor Grade and Stage and Leads to Increased Sensitivity to FGF1 in Bladder Cancer", The American Journal of Pathology, 2010, vol. 177, No. 5, pp. 2379-2386.
Tsimafeyeu et al., "Overexpression of fibroblast growth factor receptors FGFR1 and FGFR2 in renal cell carcinoma", Scandinavian Journal of Urology and Nephrology, 2011, vol. 45, pp. 190-195.
Tsimafeyeu et al., "Phase II, Multicenter, Uncontrolled Trial of Single-agent Capecitabine in Patients With Non-clear Cell Metastatic Renal Cell Carcinoma", American Journal of Clinical Oncology, 2012, vol. 35, No. 3, pp. 251-254.
Turner et al., "FGFR1 amplification drives endocrine therapy resistance and is a therapeutic target in breast cancer", Cancer Res. Author Manuscript, 2010, pp. 1-17.
Wesche et al., "Fibroblast growth factors and their receptors in cancer", Biochemocal J., 2011, vol. 437, pp. 199-213.
Xie et al., "FGFR2 gene amplification in gastric cancer predicts sensitivity to the selective FGFR inhibitor AZD4547", Clinical Cancer Research, 2013, vol. 19, No. 9, pp. 2572-2583.
Registry Copyright 2015 ACS on STN, RN 1551711-58-0 Registry, (2014).
Registry Copyright 2015 ACS on STN, RN 1549769-98-3 Registry, (2014).
Registry Copyright 2015 ACS on STN, RN 1178413-57-4 Registry, (2009).

* cited by examiner

SELECTIVE INHIBITORS INTERFERING WITH FIBROBLAST GROWTH FACTOR RECEPTOR AND FRS2 INTERACTION FOR THE PREVENTION AND TREATMENT OF CANCER AND OTHER DISEASES

CROSS-REFERENCE

The present application claims convention priority to EA Patent Application No. 201400495, filed on May 22, 2014, entitled "СЕЛЕКТИВНЫЕ ИНГИБИТОРЫ, НАРУШАЮЩИЕ ВЗАИМОДЕЙСТВИЕ РЕЦЕПТОРА ФАКТОРА РОСТА ФИБРОБЛАСТОВ И FRS2, ДЛЯ ПРОФИЛАКТИКИ И ЛЕЧЕНИЯ РАКА И ДРУГИХ ЗАБОЛЕВАНИЙ". This application is incorporated by reference herein in its entirety. The present application is a continuation of International Patent Application no. PCT/EA2014/000013, filed on Jun. 6, 2014, entitled "SELECTIVE INHIBITORS INTERFERING WITH FIBROBLAST GROWTH FACTOR RECEPTOR AND FRS2 INTERACTION FOR THE PREVENTION AND TREATMENT OF CANCER AND OTHER DISEASES". This application is incorporated by reference herein in its entirety.

SUMMARY OF THE TECHNOLOGY

The present technology relates to medicine and includes the use of inhibitors, which selectively interfere with interaction of the fibroblast growth factor receptor with FSR2, and also interaction with other components of FRS2 complex. The use of selective inhibitors described herein leads to significant increase of the antitumor efficacy compared to other inhibitors and monoclonal antibodies, toxicity reduction of the conducted treatment, possibility of using low concentration of the agent for full blocking, provide long treatment. One possible advantage of the present technology is development of a new class of medicinal agents for treatment of malignant tumors and other diseases.

BRIEF DESCRIPTION OF THE DRAWINGS

FIG. 7A is a graph showing the effect of RPT835 on phosphorylation of MAPK. FIG. 7B is a graph showing the effect of RPT835 on p70S6 kinase phosphorylation. FIG. 7C is a graph showing the effect of RPT835 on phosphorylation of mTOR. FIG. 7D is a graph showing the effect of RPT835 on AKT phosphorylation.

FIG. 9A (left and right panels) is a blot showing phosphorylation of FRS2α. FIG. 9B is a blot showing phosphorylation of the indicated intracellular kinases.

FIG. 20A is a picture of necrotic changes of the tumor (macroscopic) of a laboratory animal. FIG. 20B shows (left and right panels) extensive necrosis in the tissue of the tumor (more than 75% of the tumor is represented by massive necrosis, live tumor cells remained only on the periphery of the tumor). FIG. 20C shows (left and right panels) damage of vessels inside still vitalized tissue.

DESCRIPTION OF THE TECHNOLOGY

Figure 1:
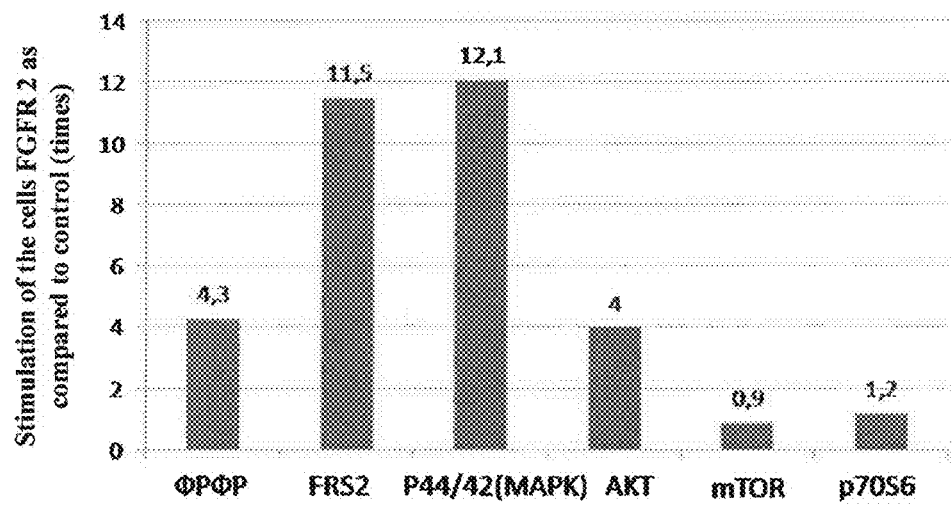
FIG. 1 is a graph showing stimulation by FGF-2 of a signal path in stomach cancer cells KATO III implemented via FGFR 2.

We know that development of malignant tumors is based on excessive proliferation of cells, and also formation of blood vessels in a tumor, through which it is fed (angiogenesis) (J. Folkman et al. Nature; 339, 58 (1989). New blood vessels are formed from already existing endothelium and is an important component of many diseases and disorders, including such ones as growth and dissemination of tumor, rheumatoid arthritis, psoriasis, atherosclerosis, diabetic retinopathy, retrolental fibroplasia, neovascular glaucoma, hemangioma, immune rejection of transplanted cornea and other tissues, and also chronic inflammations.

Proliferation of tumor cells, as well as endothelial cells can be caused by various factors which occur directly in nature. These factors bind to receptors on the surface of tumor, endothelial and other cells, which leads to activation of receptors and conducting the signal inside the cell with the subsequent According to ample data, receptors from the fibroblast growth factor (FGFR) are often expressed on tumor cells, which lead to proliferation of cells of the tumor itself and endotheliocytes, promote tumor progression. FGFR often activating mutations also change progress of disease and sensitivity to the administered therapy.

The FGFR family participates in physiological processes such as angiogenesis, migration, proliferation, differentiation and survivability of various cells.

The family counts 18 factors, which can be conditionally divided into two groups: classic (FGF1-10, 16-18 and 20) and hormone-like (FGF 19, 21 and 23) [Beenken et al. 2009]. The fibroblast growth factor (FGF) binds specifically with FGFR represented by five types. FGFR types 1-4 are standard receptors with tyrosine kinase activity, i.e. the intracellular part is represented by tyrosine kinase. The tyrosine kinase activation processes and further signal transmission inside a cell are based on the phosphorylation processes inherent for all receptors like these. Extracellular part of the FGFR consists of 3 immunoglobulin-like domains; the II and III domains contain a ligand-binding region. Due to alternative splicing, domain III changes shape and is in two states—IIIb and IIIc. This can influence on the strength of binding with ligand and activity of therapeutic agents aimed against the receptor [Eswarakumar et al. 2005; Brooks et al. 2012]. Moreover, there is information about different proliferative activity of tumor cells when FGF is bound with various subunits of domain IIIc—1α or 1β [Tomlinson et al. 2010]. FGF relates to the group of heparin-binding proteins. In order to transmit the signal to a cell and activate intracellular processes, FGF should bind with a receptor and heparan sulfate (heparin) on the surface of the cell [Abuharbeid et al. 2006]. This differs the FGF receptor activation mechanism from other factors, in particular VEGF, for which heparin sulfate is unneeded. Hormone-like FGF have a low affinity to heparin sulfate. When FGF is bound to a receptor, the main intracellular paths RAS-RAF-MAPK and PI3K-AKT-mTOR are activated with signal propagation into the core [Turner et al. 2010]. The main component of signal transmission from FGFR to intracellular kinases is FRS2 protein [Ong et al. 2000; Kouhara et al. 1997]. FRS2 is a "docking protein" activated when FGFR is bound with the ligand and forming a complex with Shp2 and Grb2, due to which the activation of FRS2 triggers activation of the both signal paths RAS-RAF-MAPK and PI3K-AKT-mTOR.

At present, a large number of target medicines blocking/inhibiting activity of various FGFR types have been created. They include inhibitors of tyrosine kinase, and also monoclonal antibodies. The existing inhibitors of tyrosine kinase decrease activity of intracellular tyrosine kinase by blocking various active parts of the same or, typically, several receptors. Non-selective blocking is associated with reduction of efficiency of the effect on tumor cells, vessel cells, and also other structures expressing the relevant type of the receptor. Efficiency of therapeutic monoclonal antibodies directed against FGFR is known to be able to considerably decrease if domain III of the FGF receptor changes shape (IIIb and IIIc) [Wesche et al. 2011; Tsimafeyeu et al. 2012]. The same happens if FGFR exists on a cell in various isoforms [Dienstmann et al. 2013]. The existing low molecular inhibitors of tyrosine kinase do not have a selective action on one type of the FGF receptor, block several types of FGF, and also other receptors. Thus, brivanib, dovatinib inhibit FGFR and receptors of growth factor of vessel endothelium [Ayers et al. 2007; Sarker et al. 2008], ponatinib, BGJ398, AZD4547, JNJ-42756493, BAY 1163877 inhibit several types of FGFR and, although to a lesser degree, but also receptors of growth factors of vessel endothelium and some other kinases [Gozgit et al. 2012; Arai et al. 2014; Gavine et al. 2012; Perera et al. 2014; Heroult et al. 2014]. Besides, cells of a certain tumor are shown to express their FGFR type (for example, kidney cancer—FGFR1 [Tsimafeyeu et al. 2011], luminal type of breast cancer—FGFR1 [Tenhagen et al. 2012], triple negative breast cancer—FGFR2 [Tannheimer et al. 2000], stomach cancer—FGFR2 [Xie et al. 2013], bladder cancer—FGFR3 [Gust et al. 2013], etc.). Consequently, simultaneous blocking of several types of FGFR is unnecessary and may lead not only to toxicity increase, but also efficiency reduction. Many works show that the existing low molecular inhibitors of tyrosine kinase in nanomolecular concentrations suppress the activity of intracellular tyrosine kinase of FGFR, yet weakly influence on phosphorylation (activity) of FRS2. In other words, interaction between FGFR and FRS2, even when the activity of intracellular tyrosine kinase of FGFR is suppressed, seems to be important, and its absence can be a factor of resistance. Thus, for example, there is no information about action of brivanib on FRS2 (Huynh et al. 2008); dovitinib influences on phosphorylation of FGFR 1/3 in nanomolecular concentration, and to a lesser degree suppresses the activity of FRS2 (Zhang et al. 2014); ponatibib, as the most selective inhibitor of FGFR, inhibits phosphorylation of FGFR with IC50 within the limits of 3-18 nmol/l, and FRS2—only 33-40 nmol/l (Gozgit et al. 2012); high-selective inhibitor AZD4547, by suppressing the activity of FGFR2 with IC50 within the limits 2 nmol/l, suppresses activity of FRS2 when using a concentration of 100 nmol/l (Gavine et al. 2012). This means that the existing inhibitors have a weak indirect inhibiting effect on FRS2, moreover do not cause interference with interaction of FGFR with FRS2.

This present disclosure describes inhibitors, the action mechanism of which includes one or more of the of the actions mentioned above and below:

1) Interference with interaction of FGFR and FRS2, which will result in reduction of phosphorylation and loss of activity by FRS2, and also, possibly, but not necessarily, disruption of interaction with other components of FRS2 complex.

2) Absence of influence on the intracellular tyrosine kinase of FGFR and phosphorylation of the receptor itself.

3) Absence of effect on the intracellular tyrosine kinase of other receptors with tyrosine kinase activity and on their phosphorylation.

4) No binding with the active center of FGFR and the active center of other receptors.

5) Selective interference with FRS2 interactions mostly with one type of FGFR, or in some cases—several types of FGFR.

Also, absence of inhibitor-determined expressed toxicity is expected as a result of selective action.

The inhibitors described in the present disclosure interfere with interaction of FGFR with FRS2, which considerably influences on FRS2 protein, the activity of which decreases (Example 1). The most important thing in the action mechanism of the described inhibitors is absence of influence on activity of the common FGFR, and also intracellular part of the receptor represented by tyrosine kinase, and absence of influence on the activity of other receptors with tyrosine kinase activity (Example 2). This characterizes highly-selective action of the inhibitors and emphasizes the importance of disrupted interaction of FGFR-FRS2 without the need to block the kinase activity of the receptor and other mechanisms. It is important to note that the described inhibitors no not interact with the active center of FGFR and do not interfere with the binding of FGFR with the ligand (Example 3).

Activity reduction of FRS2—the main conductor of the signal from the receptor to the intracellular cells, leads to suppression of the signal transduction inside the cell. Besides, the described inhibitors may not influence immediately other components of the signal paths RAS-RAF-MAPK and PI3K-AKT-mTOR, which characterizes their selective action only in relation to the interaction of FGFR and FRS2 (Examples 4, 5). For some types of described inhibitors, the action against one or several components of signal paths cannot be excluded (Example 6). However, this can be both an independent influence on the signal path component structure, and a consequence of FGFR-FRS2 blocking. Also, the described inhibitors can interfere with complex FRS2 with Shp2 and/or Grb2, which can lead to enhancement of the effect, but is not obligatory, while the main thing in limiting the signal conducting is blockage of FGFR-FRS2 interaction (Example 7). The described inhibitors may inhibit only one FGFR type as described in Example 8 for FGFR2, or several ones (Example 6). Dependence of inhibitor activity on the isoform of a certain FGFR type in most cases should be excluded (Example 9).

Such selective interference with the interaction of FGFR and FRS2 leads to the desired therapeutic effects of the described inhibitors, for example, suppression of proliferation of endothelial cell migration, formation of tubular structures of the vessel, growth of mature vessels (Examples 10 and 11), suppression of proliferation of tumor cells (Examples 12), slowdown of tumor growth (Example 13), development of necrosis in tumor (Example 14), slowdown of development of other diseases (Example 15). Selective effect of described inhibitors and absence of effect on other targets leads to reduction of apparent toxicity, which is extremely important in using therapeutic agents (Example 16).

The main objective of this invention is the use of inhibitors, which selectively interfere with interaction of fibroblast growth factor receptor with FRS2, and also interaction with other components of FRS2 complex, with the properties described above. An example of such inhibitor interfering with interaction of FGFR of the 2 type and FRS2, can be a substance defined by chemical Formula I.

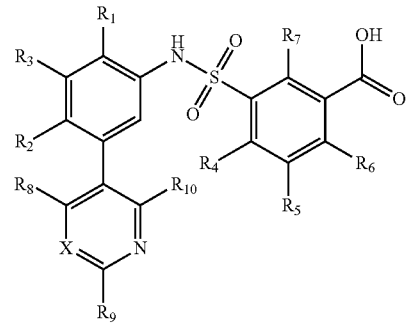

Formula I $R_1$, $R_2$, $R_3$, $R_4$, $R_5$, $R_6$, $R_7$, $R_8$, $R_9$, $R_{10}$ can be similar or different and can independently include groups —$NH_2$, —$NO_2$, —$CH_3$, —$CH_2NH_2$, —F, —Cl, —Br, —I, —$CF_3$, —$OCH_3$, —$C_2H_5$, —H, substituted or unsubstituted primary, secondary and tertiary alkyl groups, substituted or unsubstituted aryl group, substituted or unsubstituted alkenyl groups, substituted or unsubstituted alkinyl groups, substituted or unsubstituted heterocyclic groups, substituted or unsubstituted heterocyclylalkyl groups, substituted or unsubstituted alkoxyalkyl group, substituted or unsubstituted aryloxyalkyl groups, substituted or unsubstituted heterocyclyloxyalkyl groups.

X may be presented by $CH_3N$ or CH or N.

The compounds of the general formula I, can be synthesized in two stages:

stage 1—sulfonamide formation in the presence of pyridine, NaOH and ethyl acetate; stage 2—Suzuki coupling in the presence of $Na_2CO_3$, Pd $(PPh_3)_4$ and 1,2-dimethoxyethane.

Stage 1

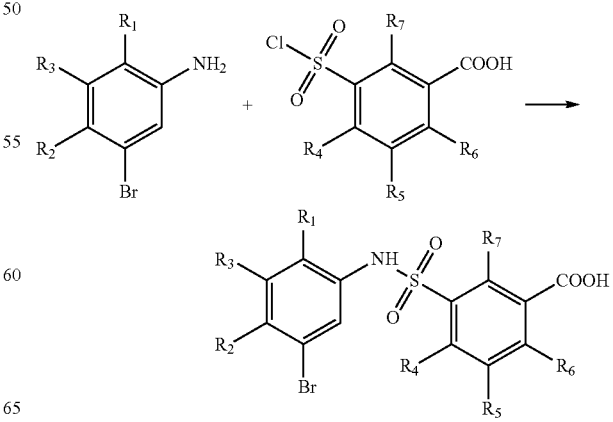

Stage 2

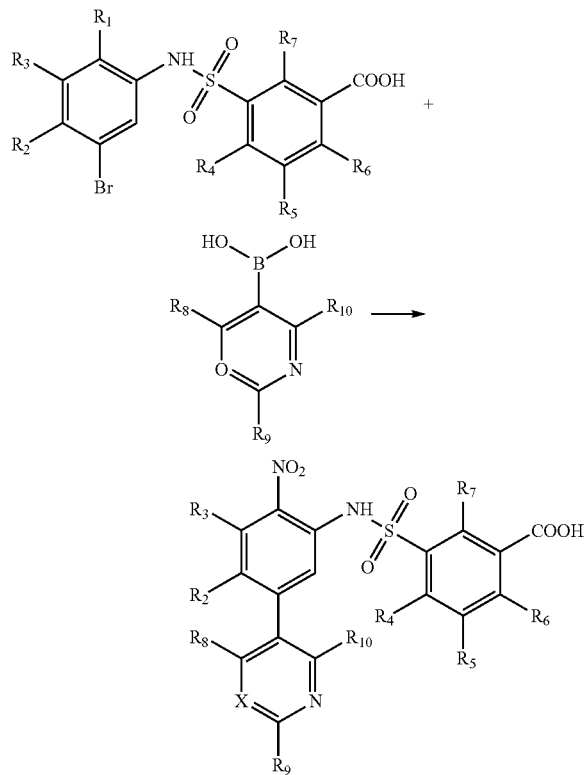

One of the examples of the compounds represented by the general formula I, the compound is 3-[N-(3,4-dimethyl-2-nitro-5(4-nitropyrimidin-3-yl)phenyl)-5-methyl-3-hlorsulfamoil]benzoic acid

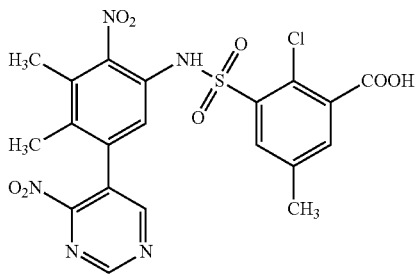

which was synthesized as follows:
Stage 1

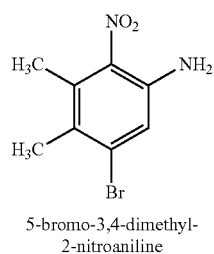

5-bromo-3,4-dimethyl-
2-nitroaniline

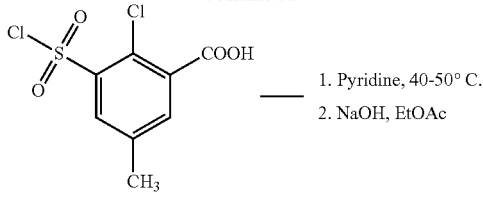

5-methyl-3-(chlorosulfonyl)-2-
chlorobenzoic acid

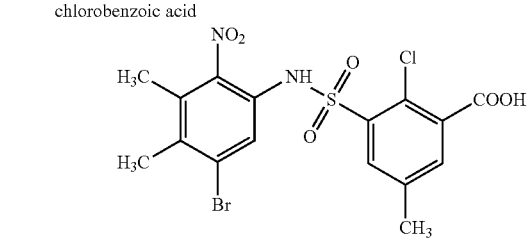

intermediate

A solution of 5-bromo-3,4-dimethyl-2-nitroaniline in dry pyridine under argon is cooled in an ice bath. 5-methyl-3-(chlorosulfonyl)-2-chlorobenzoic acid is added and the reaction is stirred for 19 hours at temperature 40-50° C. Water is added and the solvent is removed under reduced pressure. The yellow solid is taken up in water and 1M sodium hydroxide is added followed by EtOAc. After standing for a few minutes a yellow precipitate is formed. The precipitate is filtered and washed with water. Intermediate is obtained as a white solid with a yield of about 91%.

Stage 2

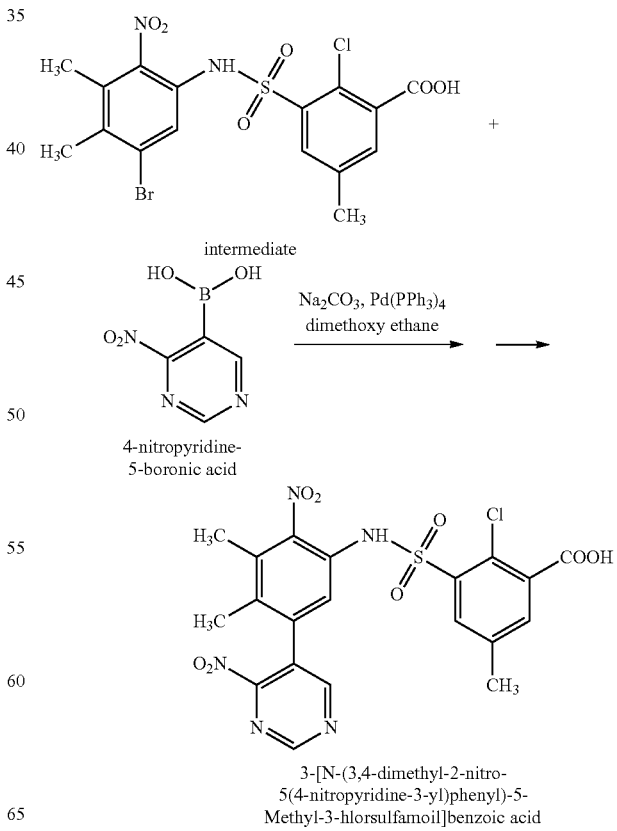

3-[N-(3,4-dimethyl-2-nitro-
5(4-nitropyridine-3-yl)phenyl)-5-
Methyl-3-hlorsulfamoil]benzoic acid A microwave reaction vessel is charged with intermediate obtained in Stage 1, 4-nitropyridine-5-boronic acid, dimethoxy ethane, water and sodium carbonate. The reaction is degassed and put under argon. Pd(PPh₃)₄ is added and the reaction is heated in the microwave for 1 h at 120° C. As the reaction is not complete after that time, the reaction is heated for another 20 min in the microwave at 120° C. The reaction is allowed to cool to room temperature, diluted with water and extracted with EtOAc. The aqueous layer is cooled in an ice bath and acidified to pH=4 with 1 M HCl. The aqueous layer is evaporated till about 1 ml and the residue is triturated with a small amount of water and brine. The product is filtered and purified via silica gel chromatography: dichloromethane/methanol 85/15 (Rf=0.3). 3-[N-(3,4-dimethyl-2-nitro-5(4-nitropyridine-3-yephenyl)-5-Methyl-3-hlorsulfamoil]benzoic acid a yellow solid is obtained in 98% purity with a yield of about 50%.

Mass spectrum (MALDI-VP): M+H 522, M+Na 544.

This compound has the properties of an inhibitor which selectively breaks the interaction of the fibroblast growth factor receptor with FRS2.

Another example of compounds of the general formula I, the compound is 3-[N-(2-nitro-5 (pyridin-3-yl)phenyl)-2-bromsulfamoil]benzoic acid

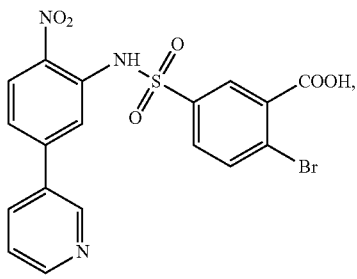

which was synthesized as follows:
Stage 1

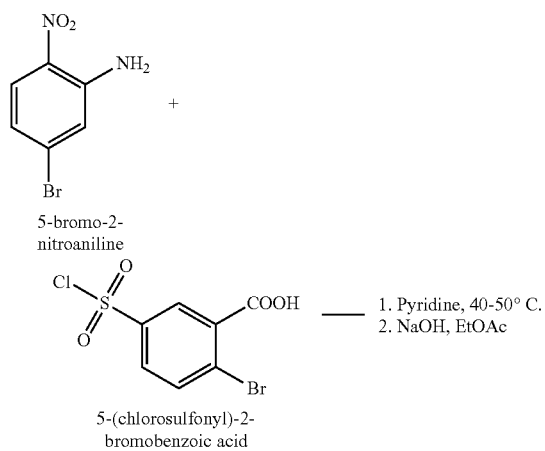

5-bromo-2-nitroaniline 5-(chlorosulfonyl)-2-bromobenzoic acid

1. Pyridine, 40-50° C.
2. NaOH, EtOAc

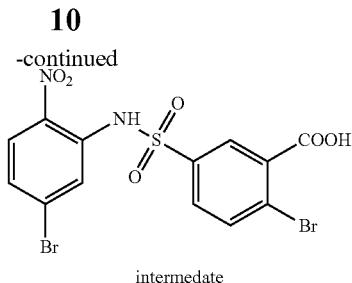

intermedate

A solution of 5-bromo-2-nitroaniline in dry pyridine under argon is cooled in an ice bath.

5-(chlorosulfonyl)-2-bromobenzoic acid is added and the reaction is stirred for 19 hours at temperature 40-50° C. Water is added and the solvent is removed under reduced pressure. The yellow solid is taken up in water and 1M sodium hydroxide is added followed by EtOAc. After standing for a few minutes a yellow precipitate is formed. The precipitate is filtered and washed with water. Intermediate is obtained as a white solid with a yield of about 90%.

Stage 2

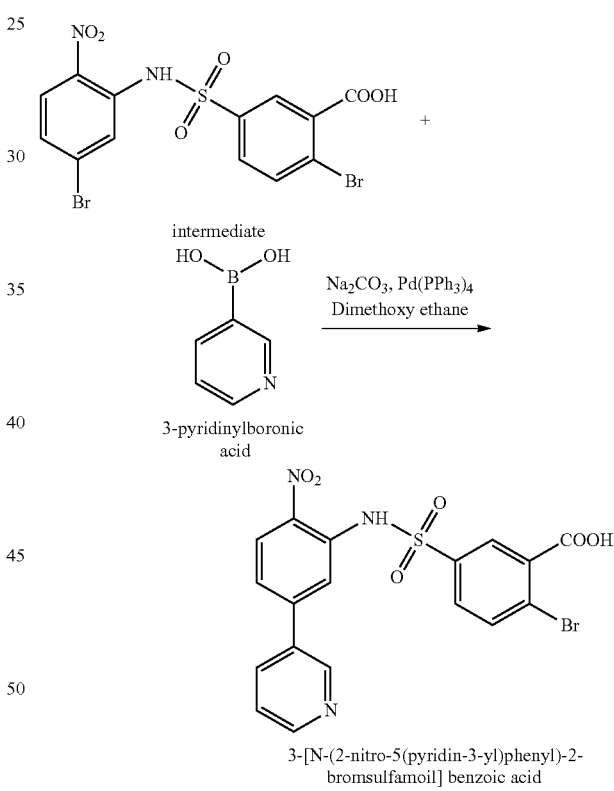

3-[N-(2-nitro-5(pyridin-3-yl)phenyl)-2-bromsulfamoil] benzoic acid

A microwave reaction vessel is charged with intermediate obtained in Stage 1, 3-pyridinylboronic acid, dimethoxy ethane, water and sodium carbonate. The reaction is degassed and put under argon. Pd(PPh₃)₄ is added and the reaction is heated in the microwave for 1 h at 120° C. As the reaction is not complete after that time, the reaction is heated for another 20 min in the microwave at 120° C. The reaction is allowed to cool to room temperature, diluted with water and extracted with EtOAc. The aqueous layer is cooled in an ice bath and acidified to pH=4 with 1 M HCl. The aqueous layer is evaporated till about 1 ml and the residue is triturated with a small amount of water and brine. The product is filtered and purified via silica gel chromatography: dichloromethane/methanol 85/15 (Rf=0.3). 3-[N-(2-nitro-5(pyridin-3-yl)phenyl)-2-bromsulfamoil]benzoic acid a yellow solid is obtained in 98% purity with a yield of about 50%.

Mass spectrum (MALDI-VP): M+H 478, M+Na 500.

This compound has the properties of an inhibitor which selectively breaks the interaction of the fibroblast growth factor receptor with FRS2.

An example of an inhibitor which selectively breaks the interaction of the fibroblast growth factor receptor with FRS2, represented by the general formula I, in the present invention can be represented by the chemical RPT835, demonstrated and Formula II relating to 3-(N-(4-methyl-2-nitro-5-(pyridin-3-yl)phenyl)sulfamoyl)benzoic acid.

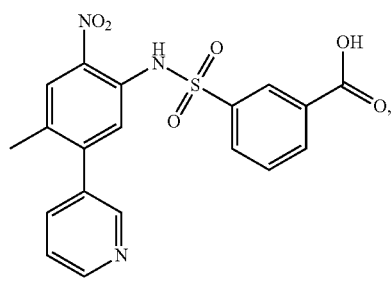

Formula II which was synthesized as follows:

Stage 1 (two load)

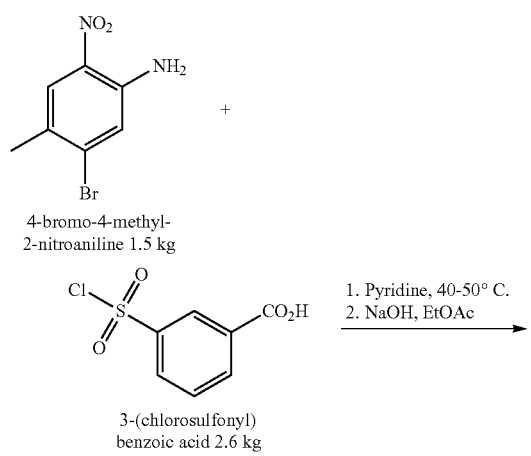

Stage 2 (two load)

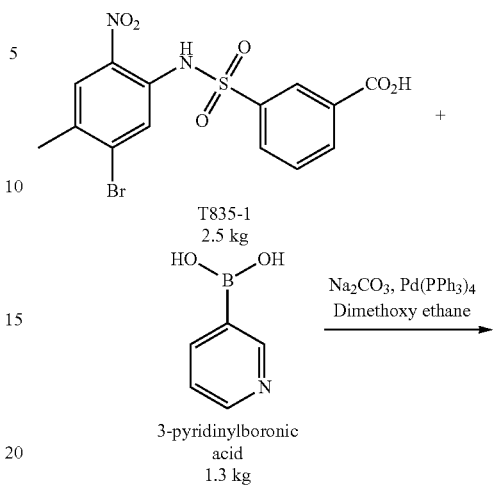

Stage 3: Cleaning (one-time fee)

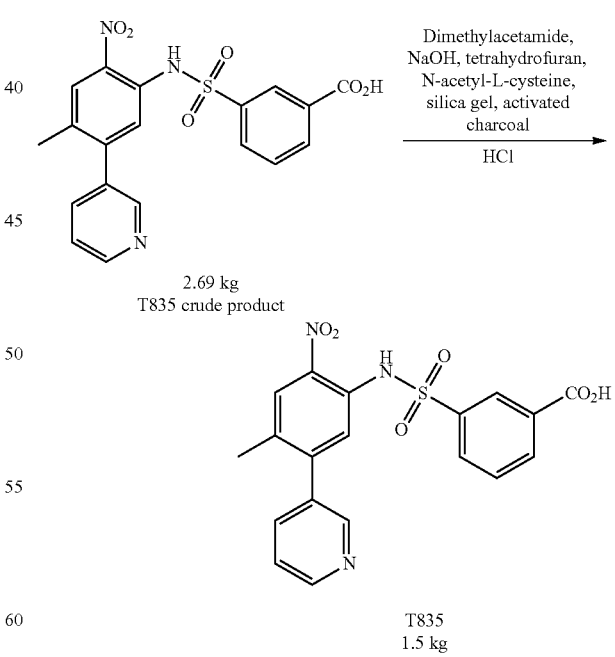

In a first step a solution of 5-bromo-4-methyl-2-nitroaniline (500 mg, 2.68 mmol) in dry pyridine (5 ml) under argon is cooled in an ice bath. 3-(chlorosulfonyl)benzoic acid (944 mg, 4.28 mmol) is added and the reaction is stirred for 19 hours at room temperature. 1 ml water is added and the solvent is removed under reduced pressure. The yellow solid is taken up in water and 1M sodium hydroxide is added followed by EtOAc. After standing for a few minutes a yellow precipitate is formed. The precipitate is filtered and washed with water. 760 mg sodium 3-(N-(5-chloro-4-methyl-2-nitrophenyl)sulfamoyl)benzoate is obtained as a white solid in 91% yield.

In a second step a microwave reaction vessel is charged with sodium 3-(N-(5-chloro-4-methyl-2-nitrophenyl)sulfamoyl)benzoate (250 mg, 0,638 mmol), 3-pyridinylboronic acid (157 mg, 1.28 mmol), dimethoxy ethane (4 ml), water (0.4 ml) and sodium carbonate (203 mg, 1.91 mmol). The reaction is degassed and put under argon. Pd(PPh$_3$)$_4$ (89 mg, 0.076 mmol) is added and the reaction is heated in the microwave for 1 h at 120° C. As the reaction is not complete after that time, the reaction is heated for another 20 min in the microwave at 120° C. The reaction is allowed to cool to room temperature, diluted with water and extracted with EtOAc. The aqueous layer is cooled in an ice bath and acidified to pH=4 with 1 M HCl. The aqueous layer is evaporated till about 1 ml and the residue is triturated with a small amount of water and brine. 132 mg of 3-(N-(4-methyl-2-nitro-5-(pyridin-3-yl)phenyl)sulfamoyl)benzoic acid (20, RPT835) a yellow solid is obtained in 98% purity with a yield of about 50%.

Mass spectrum (MALDI-VP): M+H 413, M+Na 435.

Furthermore, similar inhibitor can refer to the compound 3-(N-(4-methyl-2-nitro-5-(pyrimidin-5-yl)phenyl)sulfamoyl)benzoic acid represented by Formula III be.

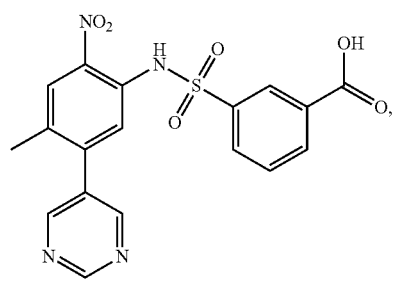

Formula III which was synthesized as follows:

Stage 1

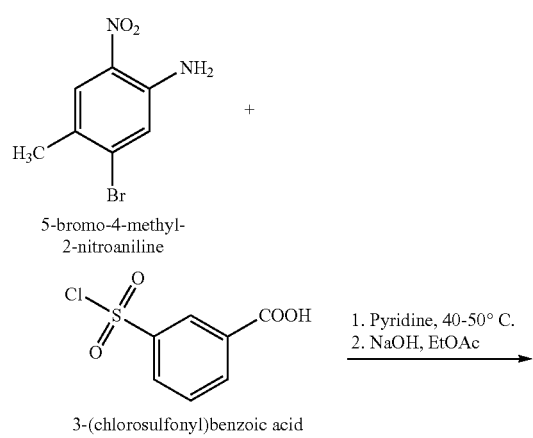

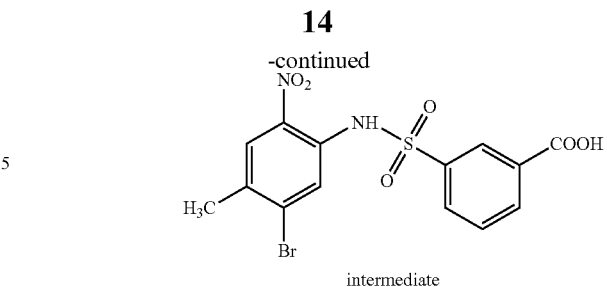

intermediate

Stage 2

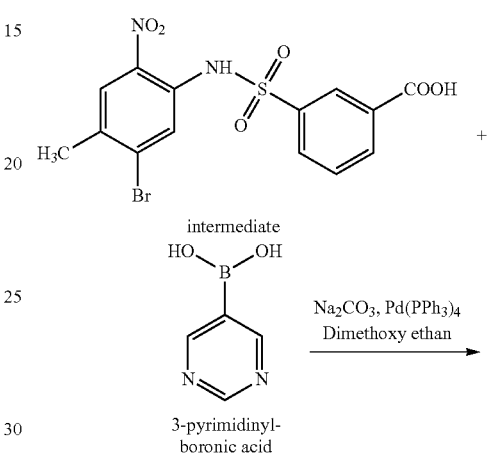

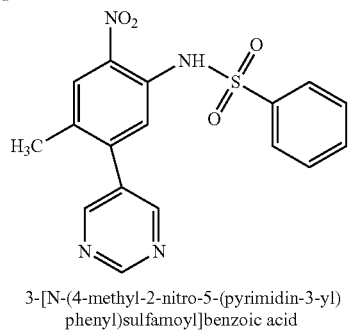

3-[N-(4-methyl-2-nitro-5-(pyrimidin-3-yl)
phenyl)sulfamoyl]benzoic acid

In a first step a solution of 5-bromo-4-methyl-2-nitroaniline in dry pyridine under argon is cooled in an ice bath. 3-(chlorosulfonyl)benzoic acid is added and the reaction is stirred for 19 hours at room temperature. 1 ml water is added and the solvent is removed under reduced pressure. The yellow solid is taken up in water and 1M sodium hydroxide is added followed by EtOAc. After standing for a few minutes a yellow precipitate is formed. Intermediate is obtained as a white solid in 91% yield.

In a second step a microwave reaction vessel is charged with intermediate obtained in Stage 1, 3-pyrimidinylboronic acid), dimethoxy ethane, water and sodium carbonate. The reaction is degassed and put under argon. Pd(PPh$_3$)$_4$ is added and the reaction is heated in the microwave for 1 h at 120° C. As the reaction is not complete after that time, the reaction is heated for another 20 min in the microwave at 120° C. The reaction is allowed to cool to room temperature, diluted with water and extracted with EtOAc. The aqueous layer is cooled in an ice bath and acidified to pH=4 with 1 M HCl. The aqueous layer is evaporated till about 1 ml and the residue is triturated with a small amount of water and brine. The product is filtered and purified via silica gel chromatography: dichloromethane/methanol 85/15 (Rf=0.3). 3-[N-(4-methyl-2-nitro-5-(pyrimidin-3-yl)phenyl) sulfamoyl]benzoic acid a yellow solid is obtained in 98% purity with a yield of about 50%.

Mass spectrum (MALDI-VP): M+H 413, M+Na 435.

The inhibitor of the invention also relates to the compound 3-(N-(5-(furan-3-yl)-4-methyl-2-nitrophenyl)sulfamoyl)benzoic acid and be represented by Formula IV,

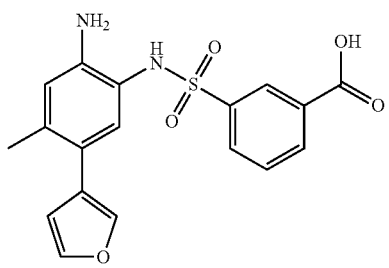

Formula IV

The inhibitor of the invention may also relate to a compound of 3-(N-(2-amino-4-methyl-5-(pyrimidin-5-yl)phenyl)sulfamoyl)benzoic acid and be described by Formula V.

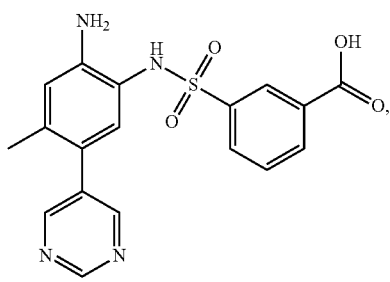

Formula V which was synthesized as follows:

The substitution reaction of the compound III NO$_2$ to NH$_2$

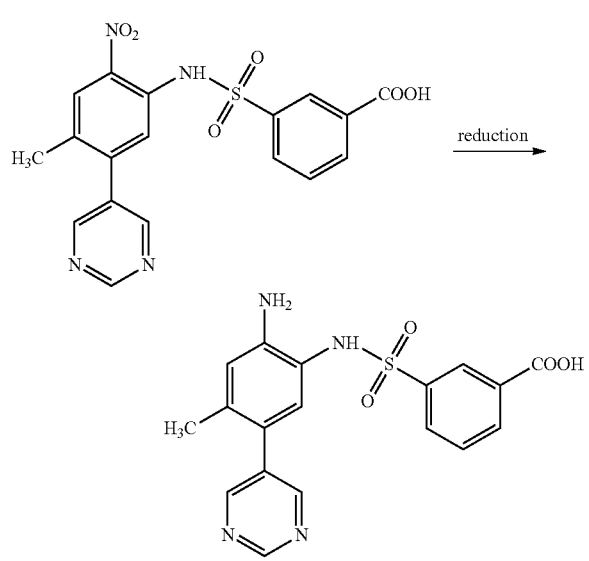 [SMILES: Cc1cc([N+](=O)[O-])c(NS(=O)(=O)c2cccc(C(=O)O)c2)cc1-c1cncnc1 ; Cc1cc(N)c(NS(=O)(=O)c2cccc(C(=O)O)c2)cc1-c1cncnc1]

For selective reduction nitro acids for amino acids can be used: Fe(OH)$_3$+NH$_3$, Fe (dust)+H$_2$O, Zn+CH$_3$COOH+H$_2$O, HCl+ZnCl$_2$, amalgam Al, HCl+Sn, FeSO$_4$/NH$_3$.

Mass spectrum (MALDI-VP): M+H 484, M+Na 506.

In addition, the inhibitor described in the invention can combine several components selected from Formulas I, II, III, IV, V. Thus, the chemical formula of such combined substance can be, for example, like this (Formula VI).

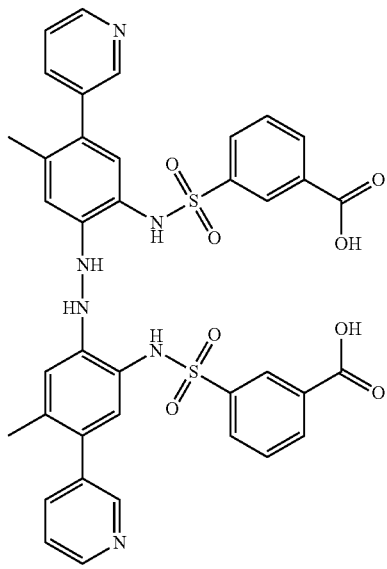

Formula VI

Inhibitor interfering with interaction of fibroblast growth factor receptor and FRS2 can be chosen from any class of substances described by Formula VII.

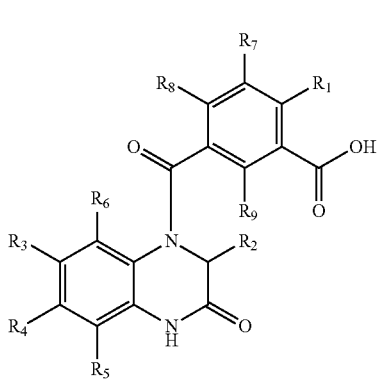

Formula VII $R_1$, $R_2$, $R_3$, $R_4$, $R_5$, $R_6$, $R_7$, $R_8$, $R_9$ moryт an be similar or different and can independently include groups —NH$_2$, —CH$_2$NH$_2$, —NO$_2$, —CH$_3$, —F, —Cl, —Br, —I, —CF$_3$, —OCH$_3$, —C$_2$H$_5$, —H, substituted or unsubstituted primary, secondary and tertiary alkyl groups, substituted or unsubstituted aryl group, substituted or unsubstituted alkenyl groups, substituted or unsubstituted alkinyl groups, substituted or unsubstituted heterocyclic groups, substituted or unsubstituted heterocyclylalkyl groups, substituted or unsubstituted alkoxyalkyl group, substituted or unsubstituted aryloxyalkyl groups, substituted or unsubstituted heterocyclyloxyalkyl groups.

The simplest example of chemicals pertaining to the class according to Formula VII can be 3-(3-oxo-1,2,3,4-tetrahydroquinoxaline-1-carbonyl)benzoic acid (Formula VIII) and 3-(2-methyl-3-oxo-1,2,3,4-tetrahydroquinoxalyne-1-carbonyl)benzoic acid (Formula IX).

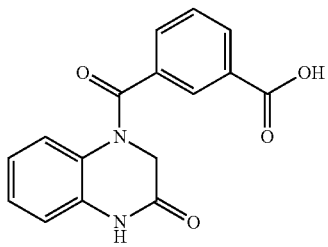

Formula VIII

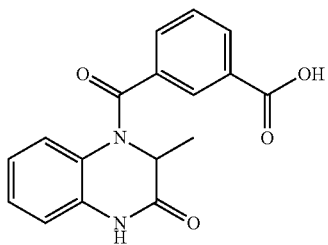

Formula IX

Inhibitor interfering with the interaction of the fibroblast growth factor receptor and FRS2 can also be chosen from ant class of substances described by Formula X.

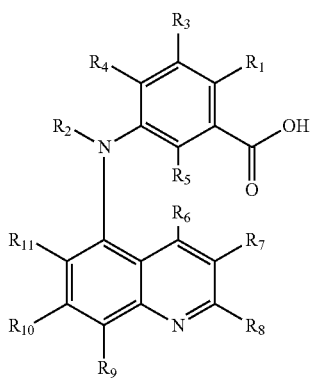

Formula X $R_1$, $R_2$, $R_3$, $R_4$, $R_5$, $R_6$, $R_7$, $R_8$, $R_9$, $R_{10}$, $R_{11}$ moryт an be similar or different and can independently include groups —$NH_2$, —$CH_2NH_2$, —$NO_2$, —$CH_3$, —F, —Cl, —Br, —I, —$CF_3$, —$OCH_3$, —$C_2H_5$, —H, substituted or unsubstituted primary, secondary and tertiary alkyl groups, substituted or unsubstituted aryl group, substituted or unsubstituted alkenyl groups, substituted or unsubstituted alkinyl groups, substituted or unsubstituted heterocyclic groups, substituted or unsubstituted heterocyclylalkyl groups, substituted or unsubstituted alkoxyalkyl group, substituted or unsubstituted aryloxyalkyl groups, substituted or unsubstituted heterocyclyloxyalkyl groups.

The simplest example of the chemical substance pertaining to this class can be 3-(quinoline-5-ylamine)benzoic acid with Formula XI

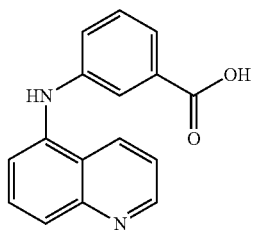

Formula XI

Also, the inhibitor can include all the structures described in formulas I-XI and represent a combined substance.

Chemical substances by formulas I, II, III, IV, V, VI, VII, VIII, IX, X, XI can be presented by pharmaceutically acceptable salt, tautomer, pharmaceutically acceptable tautomere salt and their combination.

Therapeutic Use of Inhibitors

In order to use inhibitors described in this invention, in therapeutic practice they need to be administered to a mammal, preferably a human, in the pharmaceutically acceptable form, including intravenous injection, and also by the following ways: oral, intramuscular, subcutaneous, intraperitoneal, intracerebrospinal, intra-articular, intrasynovial, intrathecal, local or inhalation. Inhibitors can also be administered by intratumoral, peritumoral, intralesional and perilesional paths to ensure local effect alongside with the systematic therapeutic effect.

Such ways of administration include pharmaceutically acceptable carriers, which by their nature have neither toxic, nor therapeutic action. Auxiliary substances, which are used for preparation of the medicine on the basis of the inhibitor described in the invention, depending on the influence on the physical and chemical characteristics and pharmacokinetics of dosage forms can be divided into the following groups:
    forming
    stabilizing
    prolonging
    solubilizing
    correcting Carriers can be used. Examples of such carriers are ion exchanging substances, alumen, aluminum stearate, lecithin, serum protein (such as human plasma protein), buffer substances, such as phosphates, glycine, sorbic acid, potassium sorbate, partial glyceride mixtures of saturated vegetable fatty acids, water, salt or electrolytes, such as protamine sulfate, disodium phosphate, dispotassium phosphate, sodium chloride, zinc salts, colloidal silica, magnesium trisilicate, polyvinyl pyrrolidone, substances with cellulose base and polyethylene glycol.

The carriers for local or gel-based forms of antagonists include polysaccharides, such as sodium salt of carboxymethylcellulose or methylcellulose, polyvinyl pyrrolidone, polyacryltes, polymers of polyoxyethylenepolyoxypropylene block, polyethylene glycol and alcohol. In all cases regular dosage forms received from warehouses are used for administration. Such forms include, for instance, microcapsules, nanocapsules, liposomes, Band-Aids, inhalation medicinal agents, aerosols, sublingual tablets and drugs with constant release of the substance.

Some suitable examples of drugs with constant release of the substance include semi-transparent matrices of solid hydrophobic polymers containing the inhibitor; such matrices have a certain form, for example they can be films or microcapsules. Examples of matrixes with constant release are polyethers, hydrogels [e.g., poly(2-hydroxyethylmathacrylate)], described by Langer et al. (J. Biomed. Mater. Res. 15, 167 (1981) and Langer (Chem. Tech. 12 (1982), or poly(vinyalcohol), poly lactides (U.S. Pat. No. 3,773,919), co-polymers of L-glutamine acid and gamma-ethyl-L-glutamate described by Sidman et al. (Biopolymers 22, 547 (1983), non-degrading ethylenevinylacetate (Langer et al. See above), degrading copolymers of lactic and glycol acids, such as Lupron Depot™ (injected microspheres consisting of polymers of lactic and glycol acids and leuprolide acetate), and poly-D-(-)-3-hydroxybutire acid. While such polymers as ethylenevinylacetate and copolymer of lactic and glycol acids are capable of constant release of molecules for more than 100 days, certain hydrogels release proteins for shorter periods of time. For the purpose of stabilization, reasonable strategies can be developed based on the acting mechanism. For example, if an aggregation mechanism expressed in formation of an inter-molecular S—S-link due to diodisulfide exchange is found, stabilization can be achieved by modification of sulfhydryl residues, lyophylisation to remove acidic solutions, humidity control, use of appropriate additives and development of specific polymeric matrix solutions.

Compounds with constant release of the inhibitor also include enclosing in liposomes. Liposomes containing inhibitors can be obtained by the methods known in this area, e.g. ones described by Epstein et al. (Proc. Nat. Acad. Sci. 82, 3688 (1985); Huag et al. (Procc. Nat. Acad. Sci. 77, 4030 (1980); U.S. Pat. No. 4,485,045 and U.S. Pat. No. 4,544,545. Liposomes normally have a small value (about 200-800 Angstrom) and belong to a single layer type, in which the content of lipids is higher than 30 mol. % of cholesterol; the selected ratio can change for selection of optimal conditions of therapy. Liposomes with a long period of circulation are covered by U.S. Pat. No. 5,013,556.

Another way of using this invention is incorporation of the inhibitor into the item, having a certain form. Such items can be used for modulation of growth the endothelium cells and angiogenesis. Besides, such products can be used for modulation of tumor and metastases invasion.

Conjugation of the described inhibitor and another treatment agent is possible. The described inhibitor can be used in various modes in combinations with other therapeutically active and/or adjuvant medicines for enhancement of the therapeutic action, and also to decrease the frequency of side effects and undesirable events.

The required dose of the described inhibitor during prevention and treatment of a disease will depend on the type of disease, degree of its severity and progress, whether the inhibiter is injected for the preventive or therapeutic purpose, the previous therapy, the patient's case record and his/reaction to the inhibitor and indications of the attending doctor. The inhibitor can be administered to the patient in various ways, simultaneously or as a series of indications, for the period of time when the inhibitor therapy is considered effective by the standard criteria of the efficiency practiced at the moment of the inhibitor indication.

The inhibitors described in the invention can be used for treatment of various neoplastic and non-neoplastic diseases and disorders. Tumors and close states, which respond to such treatment, for example, include breast cancer, non-small cells and small cells lung cancer, trachea tumor, stomach cancer, esophageal cancer, colorectal cancer, liver cancer, pancreatic cancer, gallbladder and bile passages tumor, gastrointestinal tumor, ovarian cancer, cervical cancer, endometrial cancer, endometrial hyperplasia, endometriosis, sarcoma, head and neck cancer, hepatoblastma, melanoma, skin cancer, hemangioma, cavernous hemangeoma, hemangioblastoma, adrenal cancer, retinoblastoma, astrocytoma, glioblastoma, nerve sheath tumor, oligodendroglioma, medulloblastoma, nuroblastoma, rhbdyoblastoma, leiomyosarcoma, renal cell carcinoma, bladder cancer and urothelial cancer, penile cancel, prostate cancer, Wilms tumor, germ cells tumors, neuroendocrine tumor, tumors of unidentified primary site, leucoses and lymphomas, anomaly vessel proliferation connected with phacomatoses.

There is a possibility of using the described inhibitors for non-cancer diseases, which respond to treatment including such as rheumatic diseases, cardiovascular diseases, including atherosclerosis, diseases of the respiratory system, diseases of the digestive system, kidney diseases, including glomerulonephritis, skin diseases, including psoriasis, diabetic and other retinopathies, fibroplasia, neovascular glaucoma, endocrinal diseases and metabolism diseases, transplantation of cornea and other tissues, chronic inflammations, ascite, preeclampsia, pericardial effusion (for example, connected with pericarditis) and pleural effusion, neurological diseases.

Depending on the type of the disease and on its severity degree, the initial dose to administer to a patient will be 0.001 mg/kg to 200 mg/kg, or more preferably 1 mg/kg to 100 mg/kg, or even more preferably 10 mg/kg to 50 mg/kg, and can be introduced by one or many separate prescriptions/administrations or by constant infusion. Usual daily dose can vary approximately from 1 mg/kg to 100 mg/kg and more, depending on the above-mentioned factors. For repeated prescription within several days and more, depending on the conditions, the treatment is repeated until the desired suppression of disease symptom is achieved. However other dosing modes can be used. Success of the treatment is determined by usual methods and analyses, for example methods for X-ray visualization of tumor.

In accordance with the use of the invention the efficiency of the inhibitor in prevention or treatment of the diseases can be improved by administration of the inhibitor serially or combined with another substance effective for this purpose, such for example as the factor of tumor necrosis, interferons, interleukins; monoclonal antibodies, growth factor "traps" and other inhibitors capable of neutralizing or inhibiting the activity of the growth factor of vessel endothelium and/or its receptors and/or the growth factor of hepatocytes and/or its receptors and/or epidermal growth factor and/or its receptors and/or placenta growth factor and/or its receptors and/or insulin-like growth factor and/or its receptors and/or fibroblast growth factors and/or its receptors and/or mTOR and/or other intracellular kinases, or one or more usual therapeutic agents, such as for example alkylating compounds, antibiotics, animetabolites, anthracyclines, vincaalkaloids, epipodophyllotoxins, other cytostatics. Combination of inhibitors described in the invention with anti-inflammatory medicines, препаратами для лечения cardiovascular pathology medicines is also possible. Such substances can be present in the administered composition or be administered separately. Besides, the inhibitor according to the method can be administered serially or in combination with radiological treatment.

One or more inhibitors are administered to a patient with a tumor in therapeutically effective doses, determined for example in observation of tumor necrosis or its metastatic focuses, if applicable. Such therapy continues till the further improvement stops being observed, or clinical examination shows that the tumor or its metastases disappeared. If the disease progresses, one or several above-described substances are administered or other treatment methods are used. Since efficiency of additional substances will vary, it is desirable to compare their influence on the tumor by standard screening. Repeated administration of the inhibitor and an additional agent is carried out until the desired clinical effect is achieved. Alternatively, the inhibitor(s) is introduced combined, if desired, together with additional substances. Standard therapeutic effect assessment scales are used to treat other diseases, e.g. rheumatoid diseases, with inhibitors.

Inhibitors described in the invention can be used with supporting and accompanying therapy medicines, e.g. with erythropoietis, agents stimulating leukopoesis or increasing the number of thrombocytes and/or neutrophils, macrophages, with nutritive support, non-steroidal anti-inflammatory drugs, blood components, corticosteroids, zoledronic acid, antibodies against RANKL, antiemetic drums, etc.

Several proofs of reasonability of using inhibitors described in the invention are provided below as examples. The below examples are proposed only as illustration and should not be seen as something that restricts this invention.

Example 1 (Research Results): Interference with Interaction of FGFR2 with FRS2 when Adding Inhibitor RPT835

For assessment of the effect of RPT835 inhibitor characterized in this invention with formula II, stomach cancer cells KATO III, which express FGFR2, were used for FRS2 phosphorylation. FGF-2 in concentration of 1 mg/ml and heparin 10 mg/ml were added to the cells for stimulation of FGFR. RPT835 was added in various concentrations. A part of the cells was left without adding the inhibitor, and a part of the cells—without adding either inhibitor, or stimulating agents (control group).

Two standard methods for assessment of the phosphorylation level of FGFR and FRS2:
  Western blotting using manual work;
  Automatic capillary electrophoresis and immunodetection using automatic system Wes™ (ProteinSimple; SantaClara, Calif.).

Stimulation of KATO III cells with fibroblast growth factor led to significant activity enhancement (phosphorylation) of FGFR (4.3 times), FRS2α (11.4 times), p44/42 (MAPK, 12 times) and AKT (4 times) compared to the non-stimulated cells. Phosphorylation of mTOR protein and p70S6 kinase was observed to a lesser degree (FIG. 1).

Figure 2:
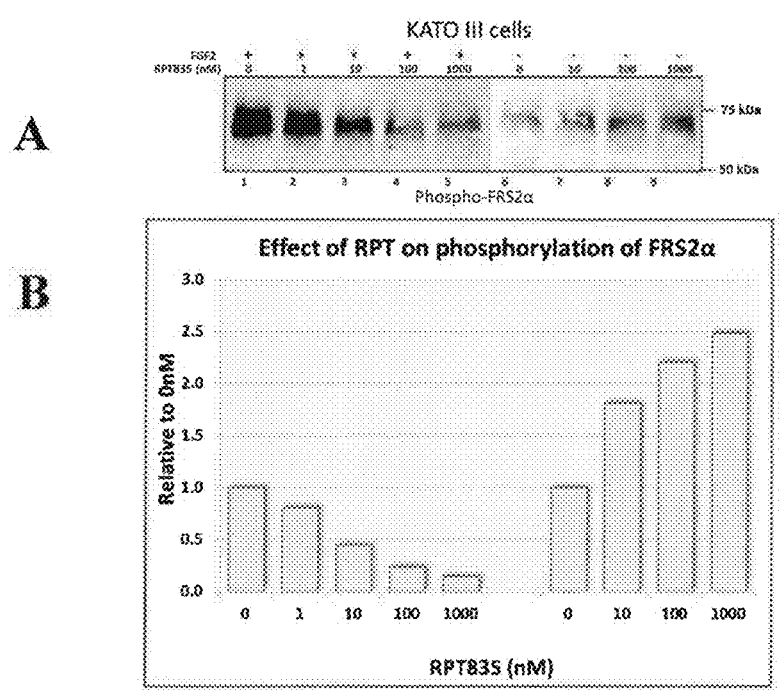
FIG. 2 shows that inhibitor RPT835, according to one embodiment of the present disclosure, leads to significant reduction of phosphorylation of FRS2. Panel A is a blot for phospho-FGF2α in KATO III cells. Panel B is a graph indicating the effect of RPT on phosphorylation of FRS2α.
Figure 3:
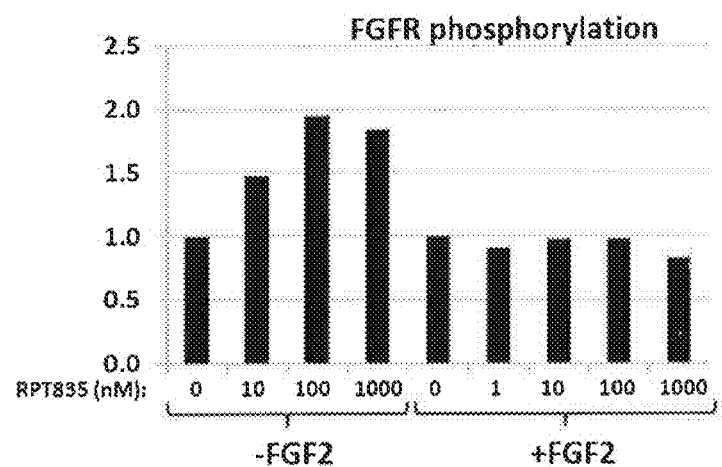
FIG. 3 is a graph showing that inhibitor RPT835, according to one embodiment of the present disclosure, does not show influence on phosphorylation of general FGFR both with and without FGF-2 stimulation.

When inhibitor RPT835 are added to the cells, interference with interaction between FGFR and FRS2 was observed, which showed itself in considerable reduction of FRS2 phosphorylation (FIG. 2, panels A and B) without influence on phosphorylation of general FGFR (FIG. 3). Moreover, concentration of the semi-maximal inhibiting of (IC50) FRS2 with the use of inhibitor RPT835 was less than 10 nM.

Based on the obtained data, we can make a conclusion that FGF stimulates the whole signal path from the FGF receptor to intracellular kinases, including interaction of FGFR and FRS2. Inhibitor RPT835 does not influence on the activity of FGFR, but leads to interference with interaction of FGFR and FRS2, which in turn affects suppression of the activity of FRS2 in the nano-molar concentration.

Example 2 (Research Results): RPT835 Inhibitor Does not Influence on Tyrosine Kinase Activity of FGFR The previous Example showed absence of influence of inhibitor RPT835 on phosphorylation of to FGFR. In this research, in order to refute the action mechanism of RPT835 as tyrosine kinase inhibitor, был оценен the level of general FGFR and phosphor-FGF was assessed before and after addition of RPT835.

Like in Example 1, stomach cancer cells KATO III strongly expressing FGFR2 were used. A part of cells stimulated FGF-2 in concentration 1 mg/ml and heparin 10 mg/ml. The other part of the cells was left without stimulation. Inhibitor RPT835 in dose 1, 10, 100, 1000 nM was added to cells. The control group left without addition of RPT835.

The level of FGFR phosphorylation was assessed using standard Western-blotting and automatic capillary electrophoresis with immune-detection and use of automatic system Wes™ (ProteinSimple; SantaClara, Calif.).

Figure 4:
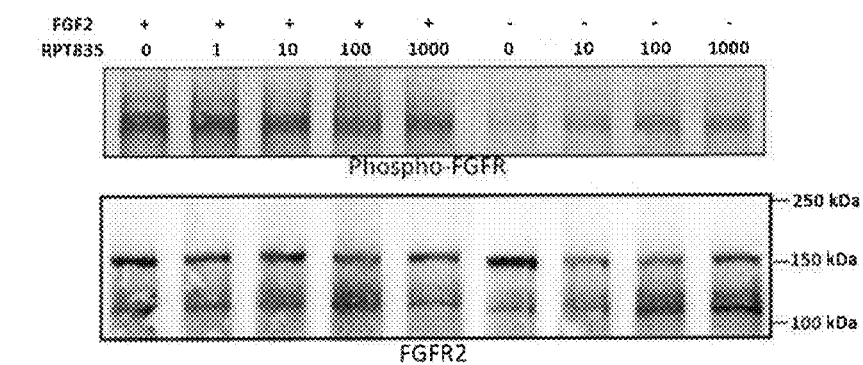
FIG. 4 shows that inhibitor RPT835, according to one embodiment of the present disclosure, does not suppress tyrosine kinase activity of FGFR2. Panel A shows a blot for phospho-FGFR and panel B shows a blot for FGFR2.

Inhibitor RPT835 did not have any effect on phosphorylation of FGFR2 stimulated by FGF-2 (FIG. 4, panels A and B), i.e. it did not show the inhibiting activity on tyrosine kinase even in the maximum concentration.

Example 3 (Research Result): Inhibitor RPT835 Does not Inhibit Binding of FGF-2 with FGFR2

Non-radioactive enzyme linked FGF2 binding assay was performed in order to assess if RPT835 influences on binding of FGFR2 and ligand (FGF-2). Recombinant chimeric protein FGFR2-Fc, which consisted of human extracellular domain FGFR2α (Inc) and Fc-fragment of human IgG$_1$ was used in the binding assay of FGF-2. FGFR2α contained all the 3 immunoglobulin-like domains and represented domain IIIc FGFR2 with high affinity to FGF-2. A 96-cavity plate tablet was covered with FGFR2-Fc protein, and then the following was added into the cavities:
  1) only FGF-2
  2) FGF-2+ heparin
  3) inhibitor RPT835 in various concentrations+FGF-2+ heparin
  4) a part of the cavities remained without stimulators (FGF-2+heparin) and RPT835 (negative control).

After incubation, enzyme-linked immunoassay was carried out using the corresponding antibodies and subsequent determination of OD$_{650}$ (optic density with wavelength of 650 nm).

Figure 5:
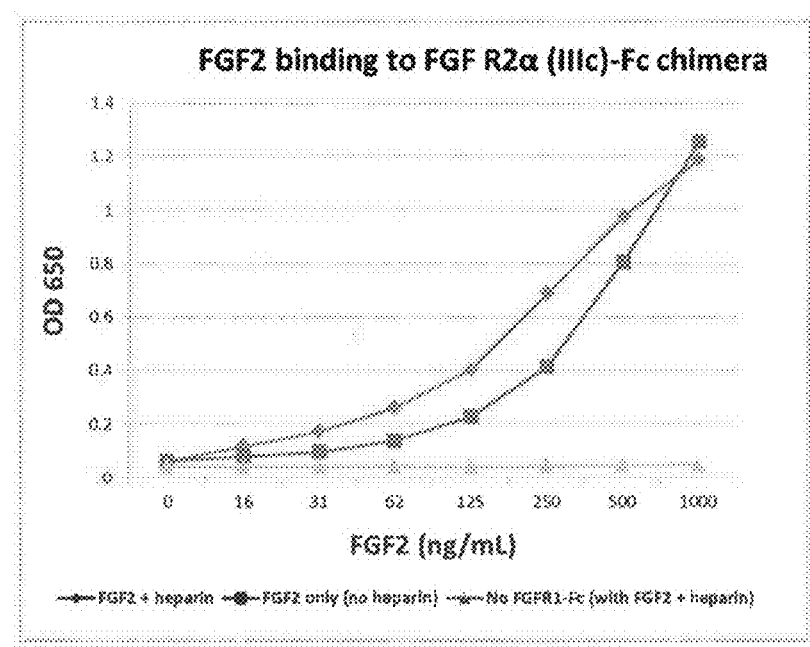
FIG. 5 is a graph showing the binding of FGF-2 with FGFR2-Fcin presence of heparin or without it.

In the first group without addition of the inhibitor and heparin, FGF-2 was shown to bind well with protein FGFR2-Fc. Binding of FGF2 with the receptor was dose-dependent. In the second group, addition of heparin improved binding of FGF-2 with the receptor. In this case, in order to achieve the same strength of binding, FGF-2 could be used in smaller doses than without heparin. In the group of negative control the signal was negative (less than 1% of the positive control). The results are presented in FIG. 5. They confirm the significance of this method: FGF-2 binds with FGFR2-Fc in the presence of heparin and without it.

Figure 6:
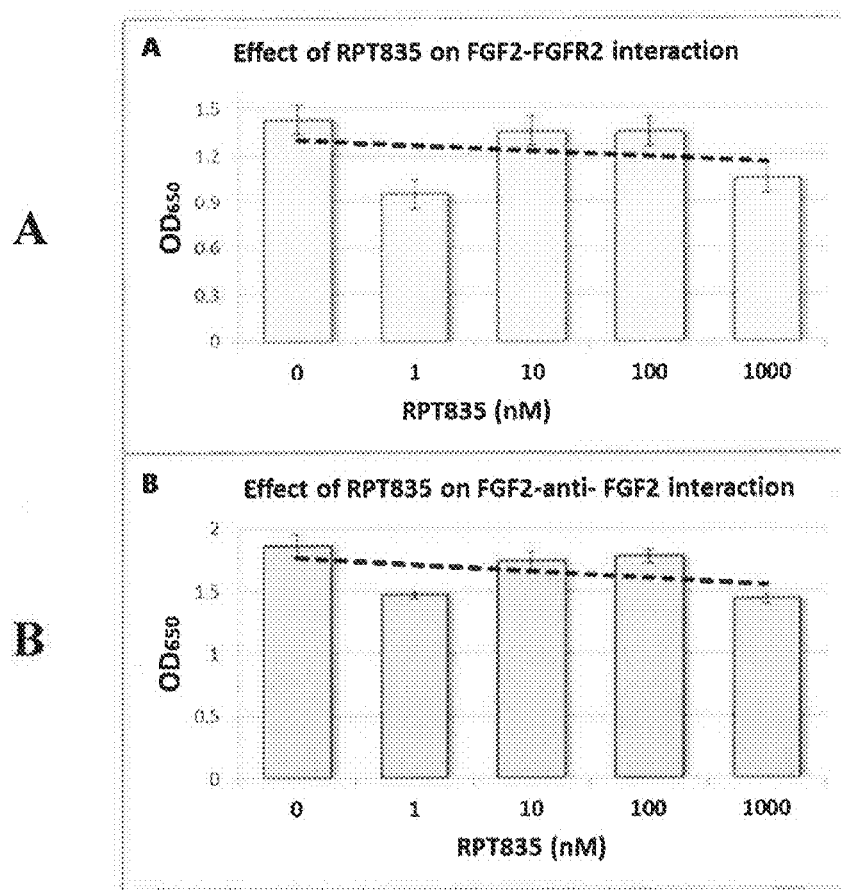
FIG. 6 shows that inhibitor RPT835, according to one embodiment of the present disclosure, does not influence on binding of FGF-2 with FGFR2-Fcoranti-FGF-2 antibody. Panel A is a graph showing the effect of RPT835 on FGF2-FGFR2 interaction. Panel B is a graph showing the effect of RPT835 on FGF2-anti FGF2 interaction.
Figure 7A:
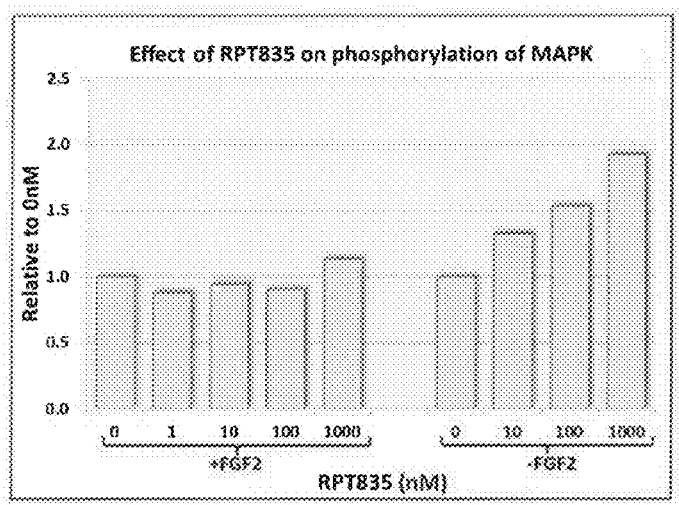
FIGS. 7A-7D show that inhibitor RPT835, according to one embodiment of the present disclosure, does not influence on phosphorylation of such intracellular kinases as p44/42(MAPK), Akt, mTOR, p70S6.
Figure 7B:
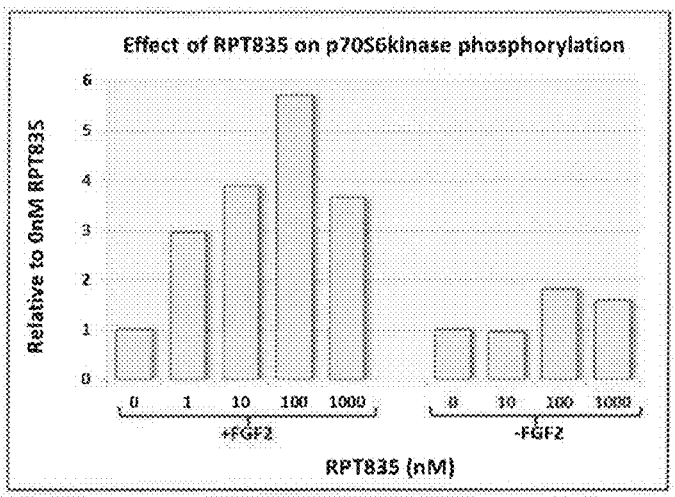
Figure 7C:
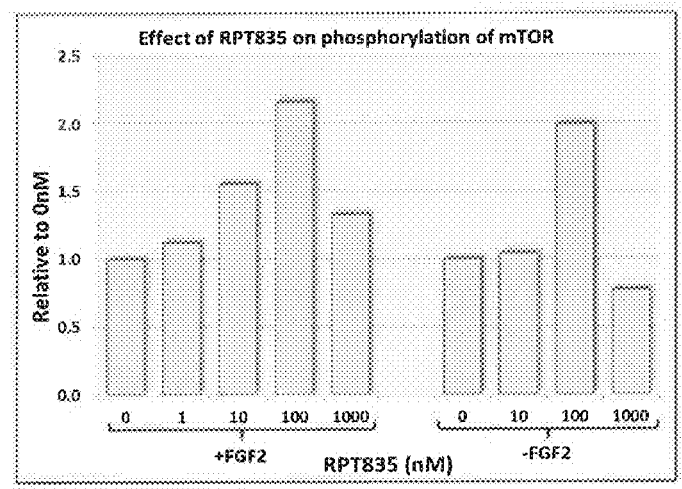
Figure 7D:
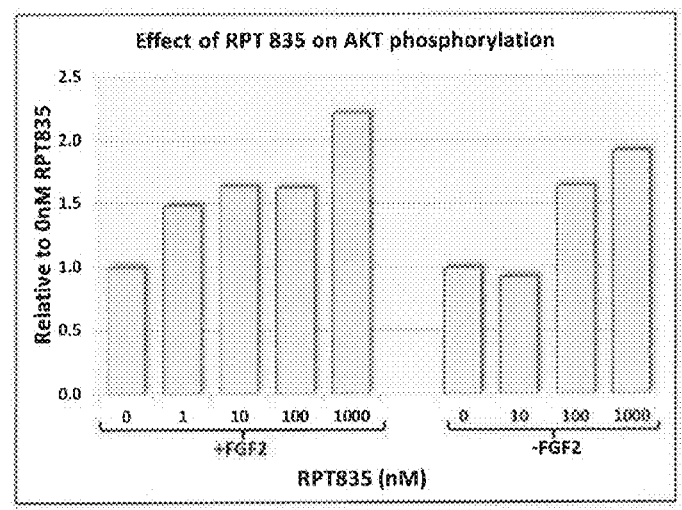

The next task was to assess influence of inhibitor RPT835 on binding of FGF-2 and FGFR2-Fc. RPT835 in concentrations of 1 to 1000 nM did not influence on binding of ligand with the receptor (FIG. 6, panel A). In order to exclude unspecific effect of RPT835 on binding, one more enzyme-linked immune assay was carried out, in which the cavities were covered with immobilized anti-FGF-2 antibody. FGF-2±RPT835 in different concentrations is added to the cavities. RPT835 in concentration of 1 to 1,000 nM did not influence on binding of FGF-2 with anti-FGF-2 antibody (FIG. 6, panel B).

Summarized results of the research prove that inhibitor RPT835 provided as an example in this invention does not interfere with binding of ligand (i.e. FGF-2) with its receptor (i.e. with FGFR2).

Example 4 (Research Results): Interference with Interaction of FGFR with FRS2 During Use of Inhibitors Determined by Formulas V, IX, XI Inhibitors V, IX, XI determined in this invention with corresponding formulas V, IX, XI, also interfere with transmission of the signal from FGFR to FRS2. By way of chemical synthesis we received the specified compounds. Stomach cancer cells Snu16 expressing FGFR2 were cultivated according to the standard method. A part of the cells was left for negative control, FGF-2 was added to the other part (positive control). Therapeutic groups included: addition of the inhibitor according to formula V and subsequent stimulation of FGF-2, addition of the inhibitor according to formula IX and subsequent stimulation of FGF-2, addition of the inhibitor according to formula XI and subsequent stimulation of FGF-2. The Western-blotting method was used for assessment of the phosphorylation level of various kinases.

Results: in cells without stimulation and without treatment, the phosphorylation levels of FGFR2, FRS2 were low (absence of phosphorylation); cells after stimulation of FGF-2 had a high level of activity of FGFR2 and FRS2 (14 and 17 times higher than in the negative control); in cells, to which the inhibitors were added, the level of FGFR2 activity did not change compared to the stimulated FGF-2 control, besides FRS2 phosphorylation was not reported (in all cases the inhibiting concentration of IC50 was less than 10 nM). Besides, the inhibitors were shown not to influence on other intracellular kinases, including Akt, Erk 1/2.

The number of cells was counted too. Cells without addition of inhibitors and FGF-2 proliferated weakly, unlike the cells, to which FGF-2 was added. As the inhibitors were added, the number of cells was comparable with the negative control group (p=0.5) and surely less than in the group with FGF-2 stimulation and without addition of inhibitors (p<0.0001).

Thus, substances described in formulas V, IX, XI are selective inhibitors of interaction between FGFR2 and FRS2, which influences on the proliferative activity of the tumor cells expressing FGFR.

Example 5 (Research Results): Assessment of Influence of Inhibitors Described in the Invention on Various Intracellular Kinases In order to prove the selective action of the inhibitors only on transmission of the signal from FGFR to FRS2 without influence on intracellular kinases, the phosphorylation level of intracellular kinases, in particular p44/42(MAPK), Akt, mTOR, p70S6.

In order to access the effect of inhibitor RPT835, characterized in his invention by formula II, on phosphorylation of the listed kinases, stomach cancer cells KATO III, which express FGFR2, was used. FGF-2 in concentration 1 mg/ml and heparin 10 mg/ml was added to the cells for stimulation of FGFR. RPT835 was added in various concentrations. Part of the cells left without addition of the inhibitor, and a part of the cells—without addition of both the inhibitor, and stimulating agents (control groups).

In order to assess the phosphorylation level, 2 standard methods were used:
Western-blotting using manual work.
Automatic capillary electrophoresis and immune-detection using automatic system Wes™ (ProteinSimple; SantaClara, Calif.).

Stimulation of cells KATO III with fibroblast growth factor led to significant enhancement of activity (phosphorylation) p44/42(MAPK, 12 times), AKT (4 times), compared to the non-stimulated cells. Phosphorylation of protein mTOR and kinase p70S6 was reported to be in a lesser degree.

As inhibitor RPT835 is added, the activity of the listed kinases did not change compared to the cells stimulated only with FGF-2 (without addition of RPT835). The phosphorylation levels are presented in FIGS. 7A-7D.

Consequently, RPT835 does not have influence on phosphorylation of other intracellular kinases.

Example 6 (Research Results): Assessment of Influence of the Inhibitor Determined by Formula VII on FGFR1, FGFR2, FGFR3, VEGFR1 and Intracellular Kinases According to the procedure described above, the phosphorylation levels of type 1-3 fibroblast growth factor receptors, FRS2, and also phosphorylation levels of VEGFR1 and intracellular kinases PI3K, p44/42(MAPK), Akt, mTOR were analyzed by the Western-blotting method.

Endothelial cells HUVEC, human renal cell carcinoma of Caki-1 type, stomach cancer cells KATO III were used in the research. All the mentioned cells expressed various types of the mentioned receptors. Just like in Example 5, a part of the cells stimulated FGF-2 and/or VEGF-A, a part of the cells was cultivated with the inhibitor described by Formula VIII, a part of the cells left without stimulation and treatment.

Figure 8:
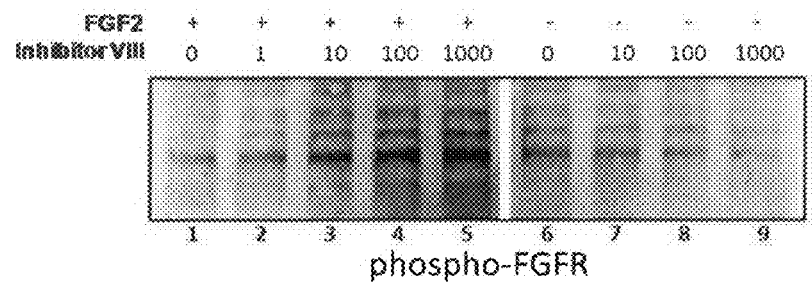
FIG. 8 is a blot showing the phosphorylation of FGFR1 using various concentrations of the inhibitor according to another embodiment of the present disclosure.

FGF-2 strongly stimulated phosphorylation of all three types of FGFR, and also PI3K, Akt and FRS2 compared with non-stimulated cells (P<0.0001 for all comparisons). VEGF-A did not have effect on FGFR of the 1-3 types and FRS2 (P>0.3 for all comparisons), but significantly increased the phosphorylation level of VEGFR1, mTOR, PI3K, MAPK (P<0.001 for all comparisons). The inhibitor by formula VIII significantly decreased phosphorylation of FRS2 (14 times, P=0.001) and PI3K (10 times, P=0.017) and weakly—FGFR2 (1.5 times) and FGFR3 (1.8 times), VEGFR1 (2.3 times). The inhibitor did not have influence on other kinases. In addition, the level of FGFR1 phosphorylation even increased (FIG. 8).

Consequently, this research demonstrates possible influence of some inhibitors interfering with interaction of FGFR2 and FRS2 on other kinases and receptors. This effect cannot be denied, and this can be connected with the main mechanisms is connected with the main mechanism—disruption of binding of FGFR and FRS2, which leads to stage-wise phosphorylation suppression of subjacent kinases. The effect on other receptors (for example, VEGFR1) is not pronounced, but it is possible just like the crossed one. The increase of the level of FGFR1 phosphorylation can be used also in the future and therapeutic during the use of inhibitors described in this invention.

Example 7 (Research Result): The Inhibitors Described in the Invention can Interfere with the Complex of FRS2 with Shp2 and/or Grb2

FRS2 is known to interact with Shp2 and Grb2, transmitting the signal to the intracellular kinases through these proteins. The purpose of this research was to prove that the inhibitors described in the invention can influence on the interaction of FRS2 with Shp2 and Grb2, but this is not the action mechanism defining them: the main mechanism is interference with interaction of FGFR and FRS2.

Stomach cancer cells Snu16 were sawn in 96-cavity plates with a size of 90 mcl/cavity. After 24 hours of incubation in a damped incubator at a temperature of 37 C, 5% $CO_2$ and 95% air to cells were the tested dissolved agent described by formula VI in the volume of 100 mcg/ml, and then FGF-2 was added as a stimulator.

After the days of cultivation by the method of automated Western-blotting, the phosphorylation level of the following proteins: FGFR2, FRS2α, FRS2β, Shp2, Grb2 was studied in the cells. After another 24 hours of the cultivation, the cells were counted.

The inhibitor according to formula VI did not suppress phosphoryllation of FGFR2 (no differences with control were found), however, it significantly, 12 times, suppressed phosphorylation of FRS2α and FRS2β (IC50<10 nM). Besides, certain suppression of Shp2 and Grb2 protein phosphorylation (more than 10 times) was noted in some cells. Therefore, the cells were divided into two groups by the phosphorylation factor of Shp2 and/or Grb2:
  group with phosphorylation suppression of FRS2 and Shp2 and/or Grb2
  group with phosphorylation suppression of FRS2 and without influence on phosphorylation of Shp2 and/or Grb2.

After the next cultivation the number of the cells equaled between the groups, and also with the control (stimulation of FGF-2, without cultivation with the inhibitor). See the results in Table 1. As you can see in the Table, the inhibitor significantly suppressed proliferation of tumor cells compared to the control regardless of the phosphorylation of Shp2 and/or Grb2.

Example 8 (Research Result): Selective Interference with Interaction of FGFR2 with FRS2 Inhibitor RPT835 is Added The purpose of this research was assessment of specific action of inhibitor RPT835 specified in this invention with formula II, on interaction of FGF2 and FRS2 and assessment of influence on interaction of other types of FGFR and FRS2. For the experiment, 2 cell lines were selected:
  stomach cancer KATO III, expressing FGFR2, and
  breast cancer MDA MB 134, expressing FGFR1.

The research procedure was the same as in the previous examples: the cells were cultivated in presence of RPT835 followed by stimulation with FGF-2 and heparin. The other part of the cells was cultivated in presence of RPT835. Phosphorylation of FGFR1 (in breast cancer cells) and FGFR2 (in stomach cancer cells), and also FRS2a (in the both cell lines) and some intracellular kinases (in breast cancer cells) was assessed using manual and automated Western blotting.

In cells KATO III, inhibitor RPT835 completely decreased phosphorylation of FRS2α (FGFR2 system) to the initial level in a dose of 100 nM. Suppression of FRS2α phosphorylation more than by 50% was observed in concentration of 10 nM (FIGS. 2A-2B). In this case, no influence on the kinase activity of the receptor itself was observed (FIG. 3).

Figure 9A:
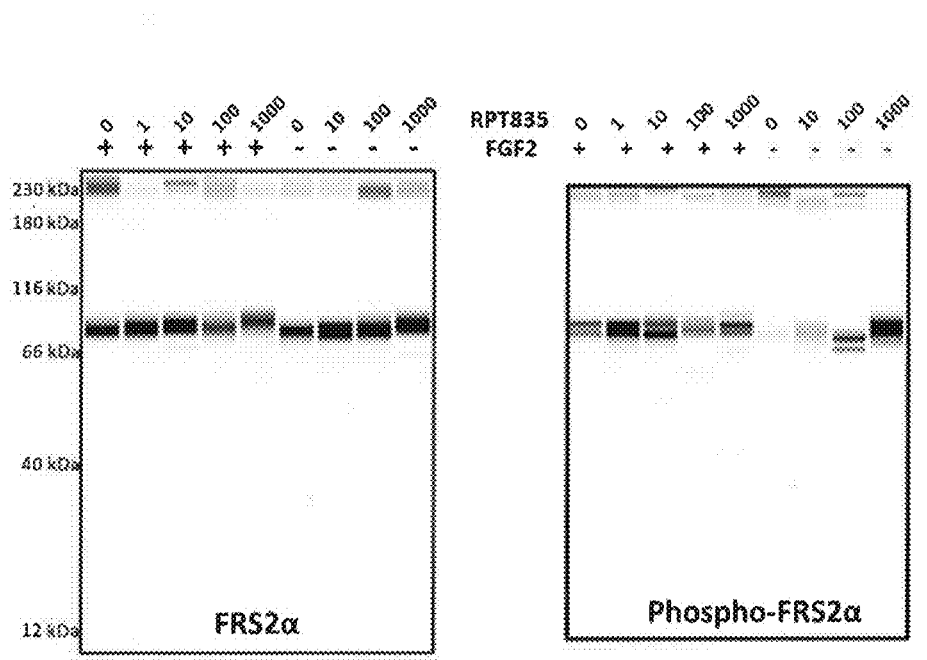
FIGS. 9A-9B show that inhibitor RPT835, according to one embodiment of the present disclosure, does not influence on phosphorylation of FRS2α, general FGFR1, intracellular kinases both with and without FGF-2 stimulation.
Figure 9B:
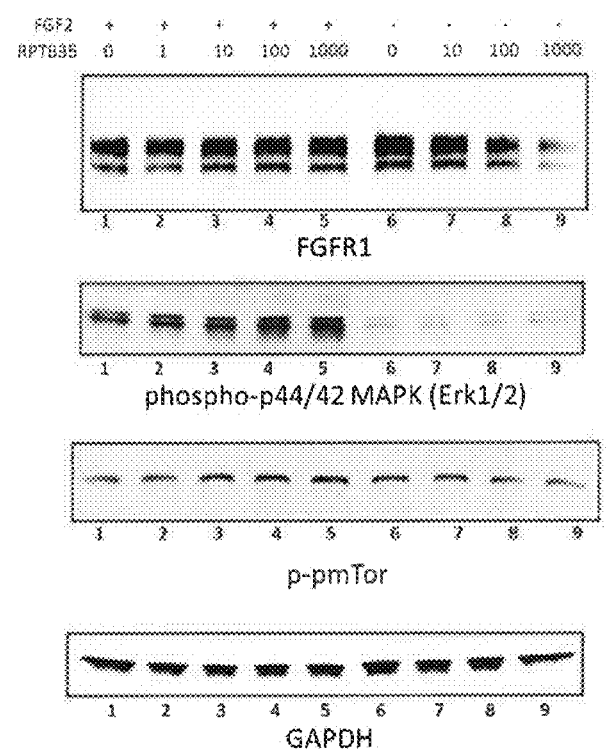

In breast cancer cells MDA MB 134, inhibitor RPT835 did not have influence on phosphorylation of FRS2α (system FGFR1), as well as for FGFR1 itself, and also intracellular kinases (FIGS. 9A-9B). As you can see in the FIGS. 9A-9B, some insignificant increase of the phosphorylation level for some intracellular kinases and FGFR1 was noted.

TABLE 1

Differences in proliferation of stomach cancer cells Snu16 from the degree of phosphorylation suppression of intracellular kinases with by the inhibitor determined by Formula VI of this invention

| Groups | Control group | Comparison with group Group with phosphorylation suppression of FRS2 and Shp2 and/or Grb2 | Group with phosphorylation suppression of FRS2 and without influence on phosphorylation of Shp2 and/or Grb2 |
|---|---|---|---|
| Control group | — | Pronounced proliferation, P < 0.0001 | Pronounced proliferation, P < 0.0001 |
| Group with phosphorylation suppression of FRS2 and Shp2 and/or Grb2 | suppression, P < 0.0001 | — | No differences, P = 0.8 |
| Group with phosphorylation suppression of FRS2 and without influence on phosphorylation of Shp2 and/or Grb2 | suppression, P < 0.0001 | No differences, P = 0.8 | — |

Consequently, the defining factor having the inhibiting effect on proliferation of tumor cells is interference with interaction of FGFR and FRS2. In this case, the level of phosphorylation of Shp2 and/or Grb2 can be different, which does not influence on suppression of proliferative activity by the inhibitor described in the invention.

Therefore, this example confirms the selective action of inhibitor RPT835 and its activity in system FGFR2. Inhibitor RPT835 influences only on interference with interaction of FGFR2 with FRS2 and does not influence on interaction of other types of FGFR with FRS2.

Example 9 (Research Results): Inhibitors Described in this Invention Show Activity Regardless of FGFR Isoform It is known that emergence of various isoforms of FGFR can influence on the therapeutic activity of medical agents blocking these receptors. The objective of this research was to prove that the inhibitors described in this invention show activity in relation to any isoforms within one type of FGFR.

The research assessed the influence of inhibitor RPT835 determined by formula II of this invention, intervention with interaction of FGFR2 represented by two most frequent isoforms IIIb and IIIc with FRS2. For this, human cell line of embryonal osteoblasts (hFOB) expressing only FGFR2 Inc, and human cell line of breast cancer SUM-52 expressing FGFR2 IIIb (all main versions of isoform—C1, C2, C3) were chosen.

Cells were divided into the groups:
1a) hFOB
1b) hFOB, stimulating FGF-1 (100 ng/ml)
1c) hFOB, cultivation with RPT835 (1 micron) and stimulation of FGF-1 (100 ng/ml)
2a) SUM-52
2b) SUM-52, stimulation of FGF-1 (100 ng/ml)
2c) SUM-52, cultivation with RPT835 (1 micron) and stimulation of FGF-1 (100 ng/ml)

Figure 10:
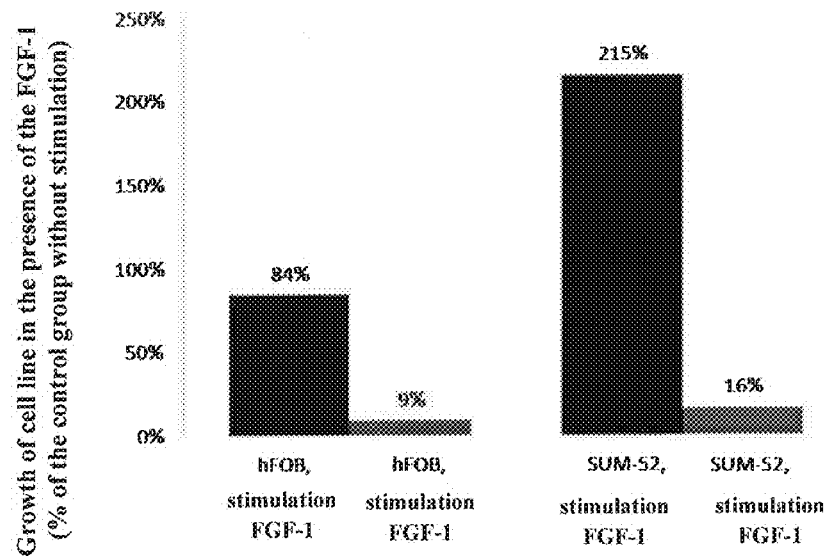
FIG. 10 is a graph showing proliferation of cells expressing FGFR2IIIborIIIc during cultivation with inhibitor RPT835, according to one embodiment of the present disclosure.
Figure 11:
FIG. 11 is a blot showing that inhibitor RPT835, according to one embodiment of the present disclosure, leads to significant phosphorylation decrease of FRS2a in cell lines expressing FGFR2 IIIborFGFR2 IIIc (assessment by the Western blotting method).

Inhibitor RPT835 reliably suppressed proliferation of cells of the both lines, expressing FGFR2 IIIc or FGFR2 IIIb (FIG. 10). There were no meaningful differences between these groups during assessment of FRS2α phosphorylation level either—the inhibitor completely suppressed the phosphorylation (FIG. 11).

Consequently, inhibitor RPT835 described in this invention, shows activity in relation to any isoforms within the limits of one type of FGFR.

Example 10 (Research Results): Antiangiogenic Activity of Inhibitors Described in this Invention Eighteen hybrid mice of the 1 generation F1 (C57B1/6× DBA/2), males with a weight of 22-30 g are used in the research. The mice (nomenclature number м02.13.00011) were received from a branch of nursery "Stolbovaya". The method described earlier was used in the experiment [Passaniti A., 1992]. The control and experiment groups had at least 3 mice. Aliquots (1,000 mcl) of Matrigel (BD Biosciences) containing heparin 60 conventional units/ml, VEGF (200 ng/ml, BD Biosciences) or bFGF (100 ng/ml, BD Biosciences) were prepared on ice. Matrigel containing heparin 60 conventional units/ml was used as negative control. Matrigel was injected in the mice subcutaneously into the side part of the back. After injection, Matrigel quickly forms single, hard gel-like implant. A weight of the inhibitor was dissolved in DMSO to concentration of $10^{-2}$M. Aliquots were frozen down to −20° C. and unfrozen immediately before injection. Refreezing of the solution was not allowed. The tested and standard objects were administered intraperitoneally on the 0, 3 and 6 day of Matrigel impintation: Bevacizumab in a dose of 10 mg/kg and RPT835-15 mg/kg. Description of the groups was presented in Table 2. Seven days after administration of Matrigel, the mice were put into sleep with diethyl ether to remove the implant. The implants were fixed for 24-36 hours in 10% neutral formalin and enclosed in paraffin for further histological research.

TABLE 2

Description of control and test groups in the experiment to study antiangiogenic properties of inhibitor RPT835 (Formula II in this invention)

| No. | Group | Description |
|---|---|---|
| 1 | Negative control | Matrigel without growth factors |
| 2 | Positive control 1 | Matrigel + bFGF |
| 3 | Positive control 2 | Matrigel + VEGF |
| 4 | Bevacizumab 1 | Matrigel + bFGF + Bevacizumab |
| 5 | Bevacizumab2 | Matrigel + VEGF + Bevacizumab |
| 6 | Inhibitor RPT835 | Matrigel + bFGF + RPT835 |

Subcutaneous injection of 1,000 mcl of Matrigel not containing growth factors did not induce formation of micro-vessels and migration of stromal and endothelial cells into the implant.

Considerable increase of the number of micro-vessels, tubular structures and migrated cells in general (for all indicators $p<0.001$) was observed in an injection of Matrigel containing 100 ng/ml bFGF. A similar effect was shown after injection of 200 ng/ml of VEGF (for all indicators $p<0.001$).

Figure 12:
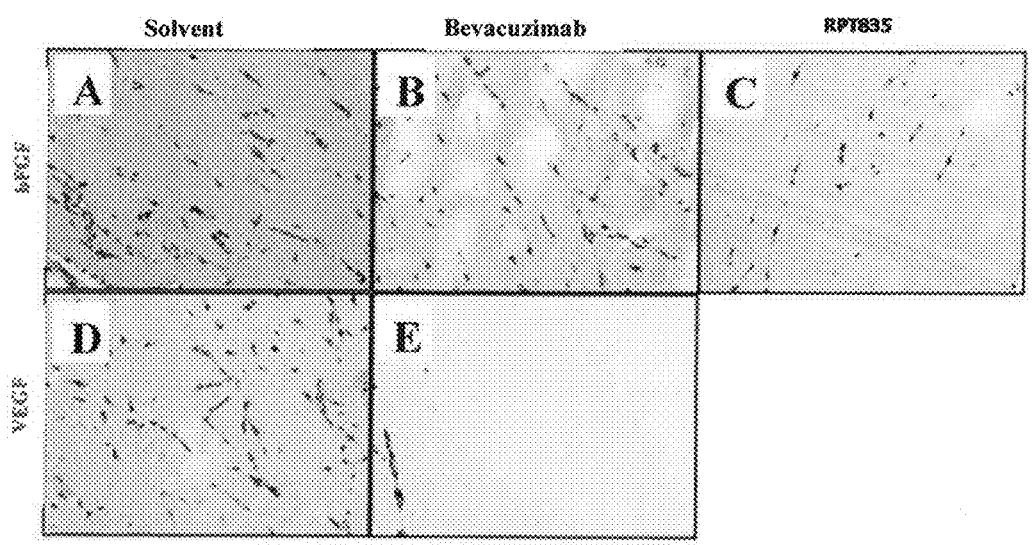
FIG. 12, panels A-E are pictures showing the influence of Bevacuzimab (10 mg/kg) and inhibitor RPT835, according to one embodiment of the present disclosure. Panels A-E show 15 mg/kg on angiogenic activity of Matrigel implants. Micro-photos of cut-offs Matrigel implants of various control and test groups. Dying with hematoxylin and eosin (zoom ×200). Panel A bFGF in solvent; Panel B bFGF in bevacuzimad; Panel C bFGF in RPT385; Panel D VEGF in solvent and Panel E VEGF in bevacuzimad.
Figure 13:
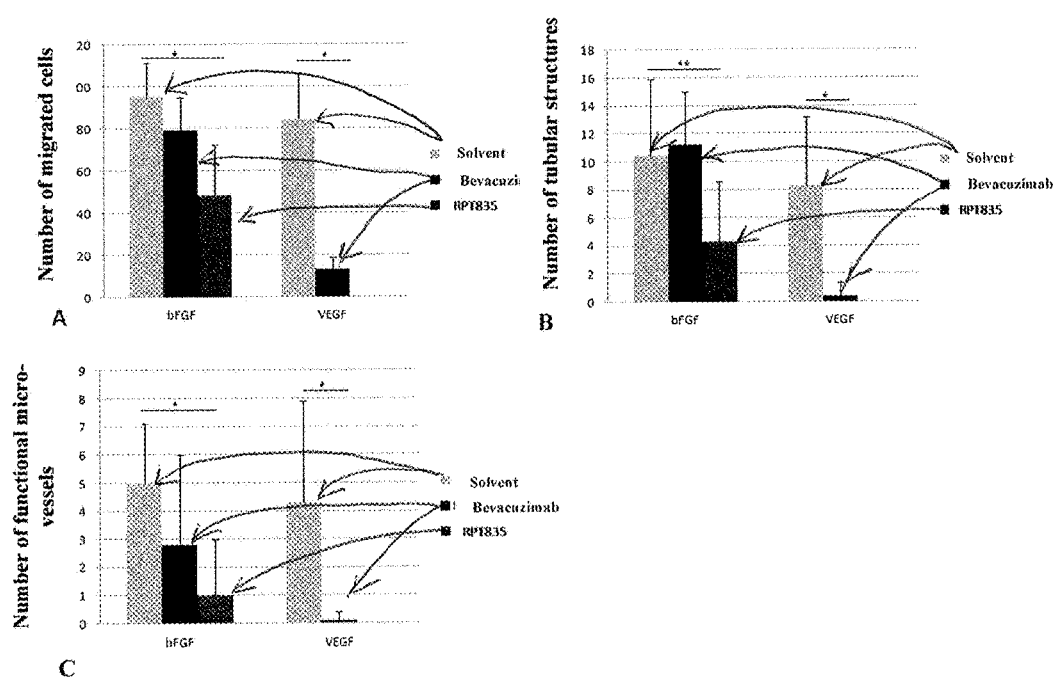
FIG. 13 shows the influence of bevacuzimab (10 mg/kg) and inhibitor RPT835, according to one embodiment of the present disclosure, (15 mg/kg) on angiogenic activity of Matrigel implants: number of migrated cells (panel A), tubular structures (panel B) and functional micro-vessels (panel C). *-p<0.001; **-p=0.016.

A considerable reduction of the number of migrated cells, tubular structures and functional micro-vessels was observed after administration of substances blocking the activity of the corresponding stimulator. Administration of bevaizumab completely blocked angiogenesis in the implants containing VEGF (for all test parameters $p<0.001$), but not angiogenesis induced by bFGF (for all test parameters $p>0.05$). Inhibitor RPT835 effectively inhibited angiogenesis stimulated by bFGF. The number of migrated cells ($p<0.001$), tubular structures ($p=0.016$) and functional micro-vessels ($p<0.001$) decreased more than 2 fold compared to the control group. The results of the research are provided in FIG. 12, panels A to E and FIG. 13, panels A to C.

Therefore, the research has established that at a triple administration in a dose of 15 mg/kg, inhibitor RPT835 statistically significantly blocks angiogenesis stimulated by bFGF. Bevacizumab in the same operation mode was effective against VEGF-stimulated angiogenesis, but not when bFGF was used.

The obtained data suggests that RPT835, as an example of inhibitors described in this invention is a promising antiangiogenic substance with a self-contained mechanism of action.

Example 11 (Research Results): Comparison of Influence of the Inhibitors Described in this Invention, and Typical Inhibitor of Tyrosine Kinase of FGFR/VEGFR—Brivanib on the Proliferative Activity of Endotheliocytes Endothelial cells HUVEC were sawn in 96-cavity plates and cultivate for 24 hours. After that, the following was added to the cells:
1) inhibitor RPT835, or
2) inhibitor described by Formula IX in this invention, or
3) brivanib—multi-kinase inhibitor of FGFR/VEGFR, and also to all cells—FGF-2 in a concentration of 25 ng/ml.

The cells were cultivated for 96 hours in general and then were calculated.

Figure 14:
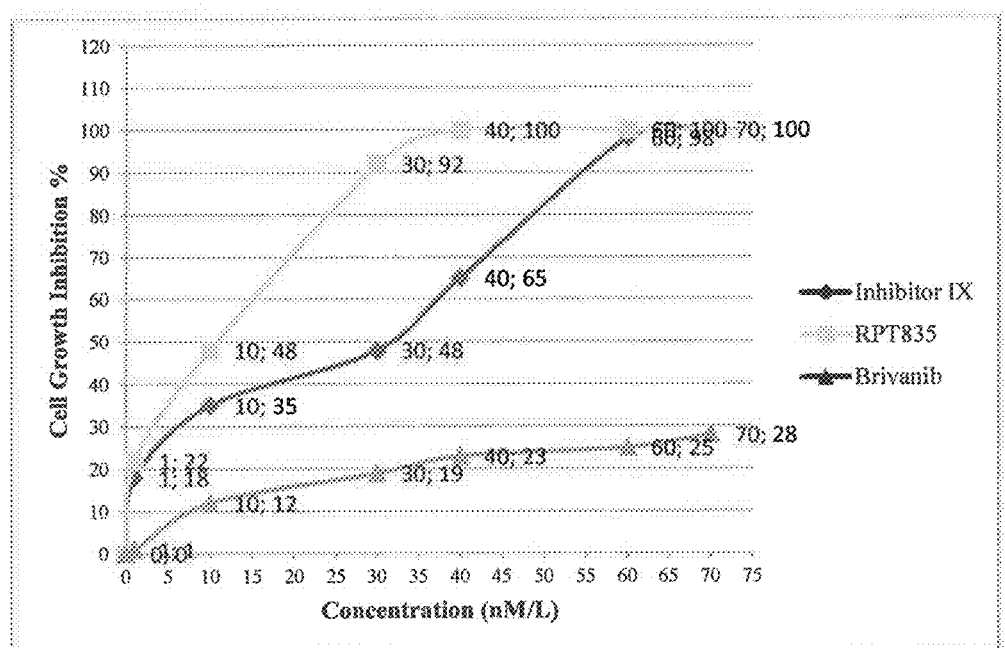
FIG. 14 is a graph showing proliferation suppression of endothelial cells HUVEC with added inhibitors as defined in the present disclosure compared to the typical inhibitor of tyrosine kinase—brivanib.

The results of the cell proliferation are presented in FIG. 14 and in Table 3 below:

TABLE 3

| | | Cell proliferation | | |
| | | Cell growth suppression, IC50, nmol/L | | |
| Cell line | FGFR2 status | Inhibitor IX | RPT835 | Brivanib |
| HUVEC | Amplification | 32 | 11 | 289 |

Inhibitors described in this invention (RPT835 and inhibitor by Formula IX) produced a pronounced anti-proliferative effect on endothelial cells unlike the typical inhibitor of tyrosine kinase of FGFR/VEGFR of brivanib.

Example 12 (Research Results): Influence of Inhibitor RPT835 on Proliferation of Tumor Cells with Various Expression of FGFR In Vitro Suppression of proliferative activity of tumor cells during cultivation with the inhibitors described in this invention has already been provided in Examples 4, 7, 9.

This research used additional cell lines: SKOV3 (ovarian cancer, ATCC # HTB-77), HS578T (breast cancer, ATCC # HTB-126), T47D (breast cancer, ATCC #HTB-1336), modified line of non-small cells lung cancer A549, line of metastatic melanoma of skin Mel Kor (RF Patent No. 2287578), and additional study of antiangiogenic activity—cell line SVEC-4-10 (endothelial cells, ATCC #CRL-2181).

The cells were cultivated in environment RPMI-1640 (PANECO) (SKOV3, HS578T, T47D, Mel-Kor) or DMEM (PANECO) (SVEC-4-10) containing 10% of embryonal serum cattle (FCS, HyClone), 2 mM glutamine (PANECO), antibiotics (100 IU/mL penicillin and 100 mg/ml streptomycin (all PANECO)) at 37° C. and 5% $CO_2$. Cells at 70-80% monolayer were used for the experiments.

The cells were planted in low density (30 t of cells/ml) in triplets on a 96-cavity plate in an environment containing 0.1% of FCS serum. On the next day, tested inhibitor RPT835 was added into the cavities in the required concentrations, and after 6 hours—the fibroblast growth factor (100 ng/ml bFGF (BD Bioscience)). The environment, antibiotics and the drugs were changed once per 3 days. Growth of cells was determined by the modified "Crystal Violet mitogenic method" for 7 days after the experiment start. The cells were rinsed with PBS, fixed with 1% parafarmaldehyde on PBS and dyed with 0.5% solution of Crystal Violet, Sigma Chemical Co on ethanol. The dye was dissolved in ethanol and measured on a spectrophotometer at 540-560 nm. The curve of cell proliferative activity inhibition was built by the dependence of the percent of the cell quantity (Y axis) on concentration of inhibitor RPT835 in the cavity of the plate (X axis). Concentration of samples, starting from which the percentage of survived cells became lower than 50% ($IC_{50}$), was calculated in program GraphPad Prizm 5. The experiments were repeated at least 3 times with three repetitions per experiment.

Figure 15:
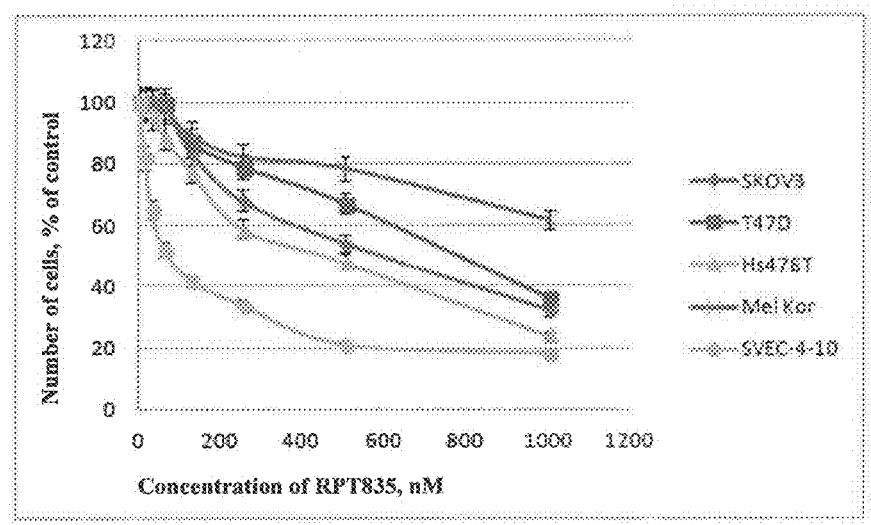
FIG. 15 is a graph showing the inhibition of proliferative activity of tumor and endothelial cells with inhibitor RPT835, according to one embodiment of the present disclosure, in vitro.

FIG. 15 shows the antiproliferative action of compound RPT835 on cultures of tumor and endothelial cells in vitro.

As you can see from the diagram, inhibitor RPT835 suppressed anti-proliferative activity of tumor and endothelial cells in various degrees. The degree of proliferation inhibiting depended on the expression status of FGFR2: the harder the receptor is expressed, the more effective was inhibitor RPT835. Thus, the maximum inhibiting effect is noted when using SVEC-4-10 line, which strongly expresses FGFR2. A moderate effect on proliferation is found in cells with low FGFK2-expression of SKOV3 and HS578T. Tested inhibitor RPT835 did not block the proliferative activity of the cell line of metastatic melanoma Mel Kor and breast cancer T47D, which hardly expressed FGFR2.

The maximum inhibiting effect was achieved during cultivation of inhibitor RPT835 with a modified line of non-small cells lung cancer A549, which had pronounced expression of FGFR2 (IC50=10 nM/L).

Thus, in study in vitro, inhibitor RPT835 was shown to produce anti-proliferative action on tumor and endothelial cells, which correlates with the expression intensity of FGFR2. This emphasizes specific activity of the inhibitor.

Example 13 (Research Results): Inhibiting of Tumor Growth In Vivo Depending on the Level of FGFR2 Expression Using Inhibitor RPT835

Females of immunodeficient mice (nude) at the age of 8 weeks were administered $2\times10^6$ tumor cells of human cell lines with various expression of FGFR2:
cell line of triple-negative breast cancer SUM52PE strongly expressing FGFR2 (purchased from Asterand, Inc. (Detroit, Mich.)
cell line of triple negative breast cancer HS578T weakly expressing FGFR2 (purchased from ATCC (CRL-125)
cell line of non-small cell lung cancer NCI-H226 not expressing FGFR2 (purchased from ATCC (CRL-5826)

After the tumor growth got established (1 $mm^3$), the mice were divided into control and treatment groups in accordance with the tumor type.

Control group 1 (N=10): SUM52PE, administration of water through a stomach tube, daily.

Treatment group 1 (N=10): SUM52PE, administration of inhibitor RPT835 through a stomach tube in a dose of 30 mg/kg, daily.

Control group 2 (N=10): HS578T, administration of water through a stomach tube, daily.

Treatment group 2 (N=10): HS578T, administration of inhibitor RPT835 through a stomach tube in a dose of 30 mg/kg, daily.

Control group 3 (N=10): NCI-H226, administration of water through a stomach tube, daily.

Treatment group 3 (N=10): NCI-H226, administration of inhibiter RPT835 through a stomach tube in a dose of 30 mg/kg, daily.

Size of tumor and weight of animals were measured every 3 day. The mice underwent euthanasia when the tumor reached the size of 2,000 $mm^3$ or on the 60 day of the experiment.

Figure 16:
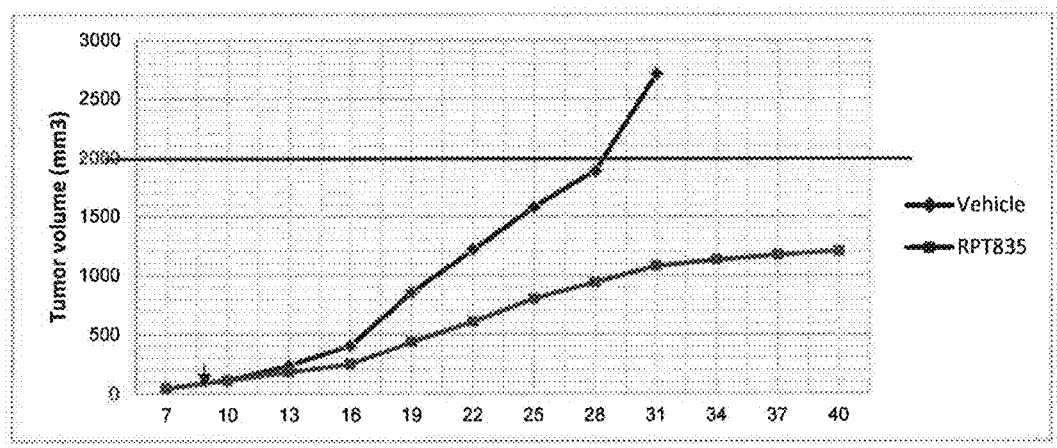
FIG. 16 is a graph showing tumor growth inhibition of triple negative breast cancer SUM52PE using inhibitor RPT835, according to one embodiment of the present disclosure, in vivo.

The diagram of tumor growth in groups 1 is presented in FIG. 16, tumor volume is in Table 4. The mice that were administered inhibitor RPT835 were noted to have significant slowdown of aggressive growth of tumor SUM52PE (P<0.000, starting from the $16^{th}$ day of the experiment). On the 30 day, the average size of the tumor in groups varied more than 2-fold and equaled in the control group 2,712.2±37 mm3, in the treatment group—1,080.7±49 mm3. Slowdown of the tumor growth was 60.2%. According to the research rules (tumor volume >2,000 mm3), the mice from the control group were subjected to euthanasia. Observation of the mice from the treatment group was continued. Stabilization of the disease (absence of tumor growth during the subsequent period of observation) was found in the group, which is evaluated as a positive effect.

TABLE 4

Size of tumor (median, mm3) in control and treatment groups 1
of triple negative breast cancer SUM52PE using inhibitor RPT835
(Formula II in this invention) in vivo.

| Day | Control (Vehicle) | Inhibitor RPT835 | Significance of difference, P |
|---|---|---|---|
| 7 | 48.0 | 48.0 | 0.775 |
| 10 | 112.0 | 112.0 | 0.316 |
| 13 | 218.5 | 181.0 | 0.032 |
| 16 | 375.0 | 256.0 | <0.0001 |
| 19 | 900.0 | 417.0 | <0.0001 |
| 22 | 1,261.0 | 591.0 | <0.0001 |
| 25 | 1,609.5 | 831.5 | <0.0001 |
| 28 | 1,875.0 | 958.5 | <0.0001 |
| 31 | 2,727.0 | 1,088.0 | <0.0001 |
| 34 | — | 1,134 | — |
| 37 | — | 1,174 | — |
| 40 | — | 1,208 | 0.167* |

*comparison between 34 and 40 days

Consequently, inhibitor RPT835 demonstrated antitumor efficacy in experiment in vivo in relation to triple negative breast cancer SUM52PE strongly expressing FGFR2.

Figure 17:
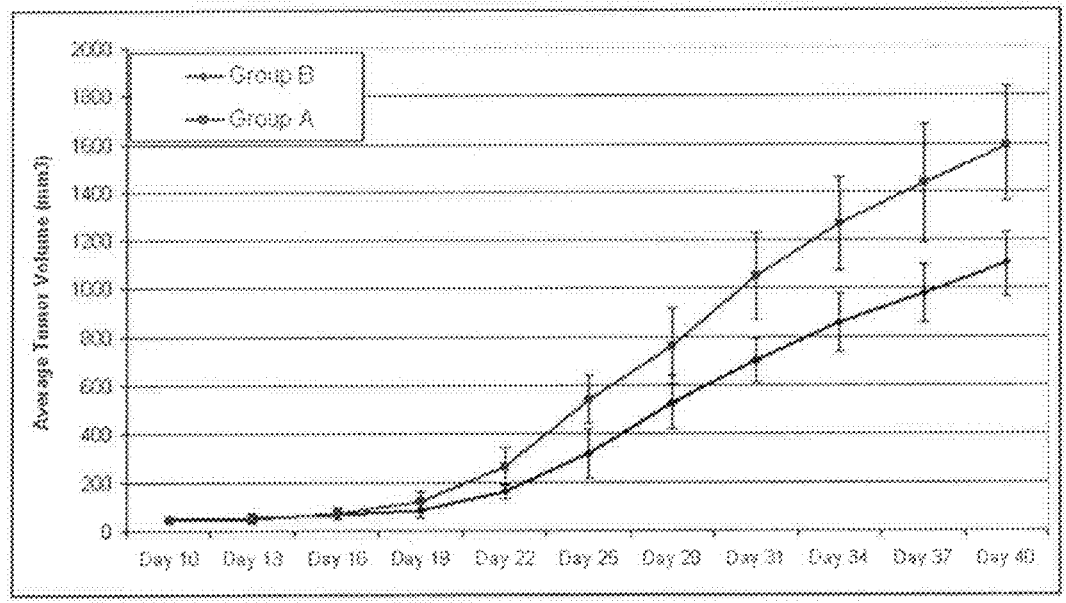
FIG. 17 is a graph showing tumor growth inhibition of triple negative breast cancerHS578T using inhibitor RPT835, according to one embodiment of the present disclosure, in vivo. Group A is control group 2 and Group B is treatment group 2.

The diagram of tumor growth in groups 2 is presented in FIG. 17.

As you can see in the Figure, inhibitor RPT835 also produced certain suppression of tumor growth of triple negative breast cancer HS578T weakly expressing FGFR2. However, the differences were less significant, than in using inhibitor RPT835 in the model of triple negative breast cancer with strong expression of FGFR2. Thus, the average size of tumor in treatment and control groups 2 by the $31^{st}$ day of research was 703±89.1 mm3 and 1,053±179.8 mm3, and by the $40^{th}$ day—1,104±162.2 mm3 and 1,592±335 mm3 (P=0.01) accordingly. Slowdown of tumor growth on the $31^{st}$ and the $40^{th}$ days was 33.2% and 30.6%.

Figure 18:
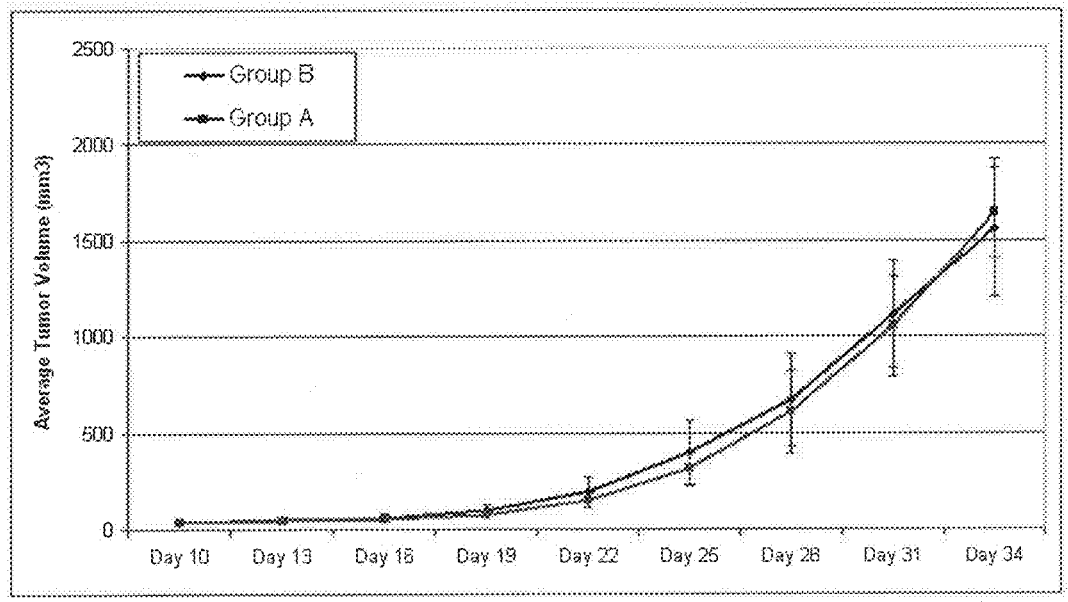
FIG. 18 is a graph showing antitumor activity of inhibitor RPT835, according to one embodiment of the present disclosure, in vivo in the model of non-small cells lung cancer NCI-H226 not expressing FGFR2. Group A is control group 3 and Group B is treatment group 3.

The diagram of tumor growth in groups 3 is presented in FIG. 18.

On the 30 day of the experiment, no significant differences in the growth of non-small cells lung cancer NCI-H226 not expressing FGFR2 were found between control and treatment groups 3: average tumor volume was 1,114±280.6 mm3 and 1,053±259.7 mm3 accordingly (P=0.619).

According to the results of research in vivo, the main conclusions were made: 1) inhibitor RPT835 provides pronounced antitumor action; 2) Tumor growth slowdown degree when using inhibitor RPT835 depends on the level of expression of FGFR2.

Example 14 (In Vivo Research Results): Inhibitor RPT835 Causes Treatment Pathomorphosis of Some Tumors Immunodefficient mice (Nude, age of the mice as of the treatment start is 8 weeks; nursery "Pushchino") were subcutaneously inoculated cells of FGFR2 of expressing line of human ovarian cancer SKOV-3. When the average tumor volume of 200 mm3 was achieved, the mice were randomized into the groups of control (standard chemotherapy with paclitaxel and caroplatin) and treatment (inhibitor RPT835). There were 10 mice in each group. Inhibitor RPT835 was assigned in a dose of 50 mg/kg, daily. The tumor volume was measured twice a week. When the tumor volume reached 2,000 mm3, the mice were subjected to euthanasia. Pathomorphosis of the tumor tissue was studied.

Figure 19:
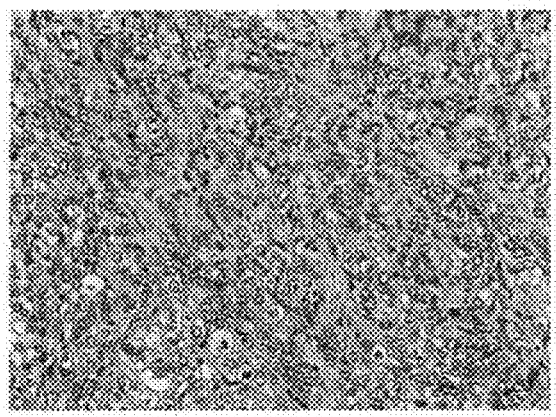
FIG. 19 is a picture showing absence of pathomorphosis in the tissue of ovarian tumor SKOV-3 in the control group (standard chemotherapy).
Figure 20A:
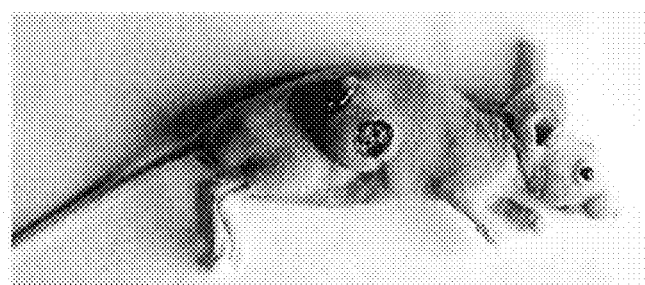
FIGS. 20A-20C are pictures showing pronounced therapeutic pathomorphosis issue of ovarian tumor SKOV-3 in the treatment group of inhibitor RPT835, according to one embodiment of the present disclosure.
Figures 20B, 20C:
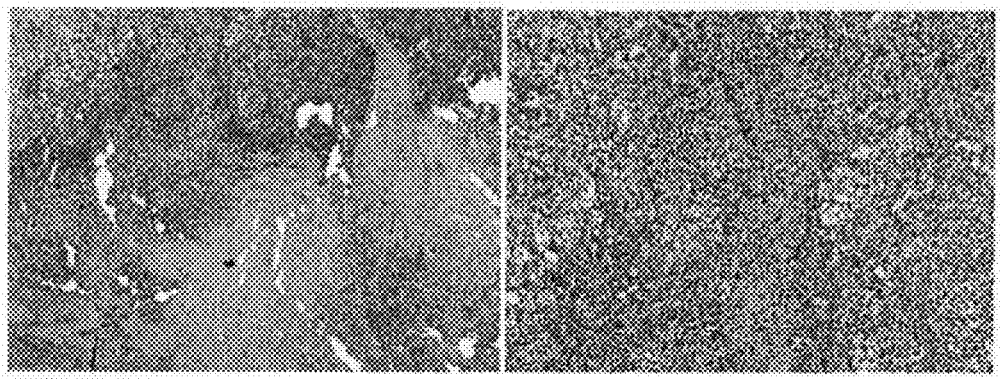
Figures 20D, 20E:
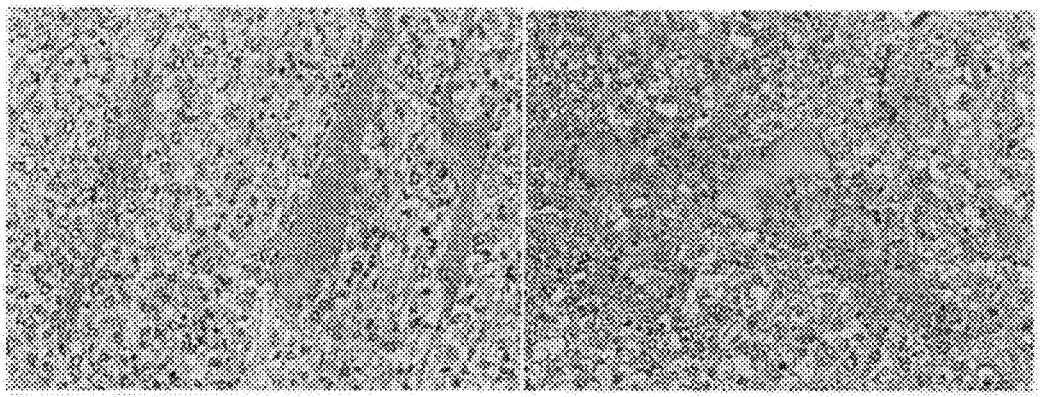
FIG. 20D and FIG. 20E show dystrophyis observed in the tumor cells.

Pathomorphosis was not found in the control group (FIG. 19). The tumor tissue was without changes.

Pronounced therapeutic pathomorphosis both macroscopic, and microscopic was observed in the treatment group when inhibitor RPT835 was used (FIGS. 20A-20E). Extensive necroses were found in the tumor (over 75% of the tumor are represented by massive necroses, live tumor cells remained only on the periphery of the tumor). Early damage of vessels inside still vitalized tissue was also observed. Dystrophy was observed in the tumor cells.

Thus, a conclusion was drawn that inhibitor RPT835 causes treatment pathomorphosis of some tumors, in particular, ovarian cancer.

Example 15 (In Vivo Research Results): Effectiveness of the Inhibitors Described in this Invention for Rheumatic Diseases Collagen-induced arthritis model was used in the research. Arthritic was induced in mice by intradermal injections of collagen of the II type combined with Freund's adjuvant. The mice were randomized into 2 groups of 5 animals in each one:

group 1: control, water through a tube for 40 days.
group 2: inhibitor described by formula III in this invention, 100 mg/kg, through a tube for 40 days.

On the 40 day, the mice were subjected to euthanasia, the tissue was studied.

Sinovitis, cartilage destruction, massive periarticular infiltration of tissue T- and B-lymphocytes, neutrophils were found in the control group.

Only insignificant infiltration with single neutrophils was found in the treatment group.

Thus, inhibitors described in the invention can be effective for rheumatic diseases and connective tissue diseases.

Example 16 (In Vivo Research Results): Inhibitors Described in this Invention are not Followed by Development of Pronounced Toxicity Toxicity of inhibitor RPT835 was assessed in in vivo studies described in Example 13. According to the standard procedure, all undesirable events were assessed, as well as loss of weight by animals, when the inhibitor is used compared to the control group. Neither weight loss, nor any undesirable side effects of the therapy was found in this research.

Besides, acute toxicity of inhibitor RPT835 was studied in the following volume in a separate research:

Acute toxicity of the medicine was researched. The results of toxicometry, data of observations of The test animals for 14 days after acute administration, and also necropsy data allow relating the medicine to the IV class of low toxicity ones (H. Hodge et al. Clinical Toxicology of Commercial Products. Acute Poisoning. Ed. IV, Baltimore, 1975, 427 p.; K. K. Sidorov, 1977). The state of the animals after acute administration testifies of good tolerability of the medicine in doses exceeding the maximal therapeutic ones (about 4.3 mcg/kg) tens—hundreds of times. Median lethal dose ($LD_{50}$) was above 2,000.0 mg/kg.

Based on the results of the macro- and microscopy, the medicine does not have an irritating effect on the mucous membrane of the gastrointestinal tract after a single administration.

According to the results of the research of the mutagenic action (chromosome aberrations), the medicine has no mutagenic properties.

The medicine does not show any allergic properties found in the reaction of immune complexes, general anaphylaxis, degranulation of mast cells and conjuctival test.

Based on the results of this research, a conclusion has been made about absence of pronounced toxicity of using inhibitor RPT835 as an example of inhibitors described in this invention.

All documents identified herein are incorporated by reference.

The invention claimed is:

1. A method for selectively interfering with the interaction between the fibroblast growth factor receptor (FGFR) and the fibroblast growth factor receptor substrate 2 (FRS2) complex in a subject comprising: administering to the subject a therapeutically effective amount of a compound of general formula I:

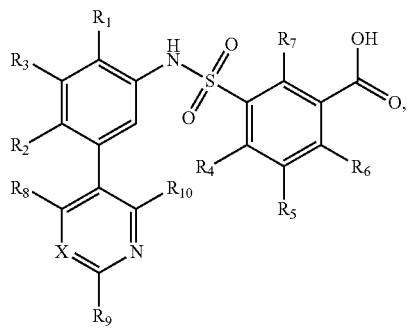

or a pharmaceutically acceptable salt thereof,
wherein $R_1$, $R_2$, $R_3$, $R_4$, $R_5$, $R_6$, $R_7$, $R_8$, $R_9$, $R_{10}$ are the same or different and are independently selected from —$NH_2$, —$NO_2$, —$CH_3$, —F, —Cl, —Br, —I, —$CF_3$, —$OCH_3$, —$C_2H_5$, —H, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclic groups, substituted or unsubstituted heterocyclylalkyl groups, substituted or unsubstituted alkoxyalkyl groups, substituted or unsubstituted aryloxyalkyl groups, and substituted or unsubstituted heterocyclyloxyalkyl groups; and
X is CH or N.

2. The method according to claim 1, wherein the compound is as set forth in formula II:

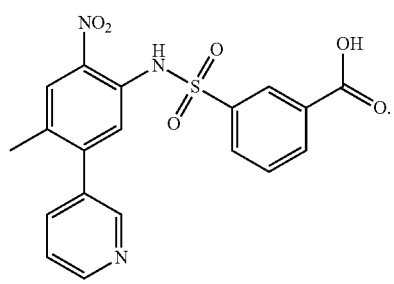

3. The method according to claim 1, wherein the compound is as set forth in formula III:

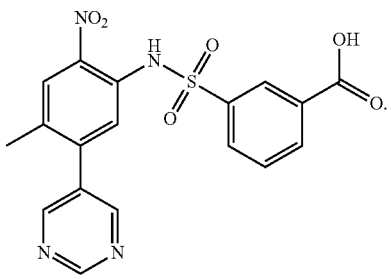

4. The method according to claim 1, wherein the compound is as set forth in formula V:

5. The method according to claim 1, wherein the compound of formula I is 3-(N-(4-methyl-2-nitro-5-(pyridin-3-yl)phenyl)sulfomoyl)benzoic acid.

6. The method according to claim 1, wherein the selective interference of the interaction between FGFR and the FRS2 complex is suppression of FRS2 activity.

7. The method according to claim 1, wherein the FRS2 complex comprises FRS2, Shp2 and Grb2.

8. The method according to claim 1, wherein the subject suffers from a cancer selected from: breast cancer, gastric cancer, lung cancer, ovarian cancer, and renal cell carcinoma.

9. The method according to claim 1, wherein the subject is in need of suppression of activity of osteoblasts.

10. The method according to claim 1, wherein the subject suffers from rheumatic diseases.

* * * * *